(12) United States Patent
Rosenstein et al.

(10) Patent No.: US 9,217,727 B2
(45) Date of Patent: Dec. 22, 2015

(54) SYSTEMS AND METHODS FOR SINGLE-MOLECULE DETECTION USING NANOPORES

(71) Applicant: The Trustees of Columbia University in the City of New York, New York, NY (US)

(72) Inventors: Jacob Rosenstein, New York, NY (US); Kenneth L. Shepard, Ossining, NY (US)

(73) Assignee: THE TRUSTEES OF COLUMBIA UNIVERSITY IN THE CITY OF NEW YORK, New York, NY (US)

( * ) Notice: Subject to any disclaimer, the term of this patent is extended or adjusted under 35 U.S.C. 154(b) by 186 days.

(21) Appl. No.: 13/787,341

(22) Filed: Mar. 6, 2013

(65) Prior Publication Data
US 2013/0180867 A1 Jul. 18, 2013

Related U.S. Application Data

(63) Continuation of application No. PCT/US2012/026292, filed on Feb. 23, 2012.

(60) Provisional application No. 61/445,918, filed on Feb. 23, 2011.

(51) Int. Cl.
| | |
|---|---|
| *G01N 27/447* | (2006.01) |
| *B82Y 5/00* | (2011.01) |
| *C12Q 1/68* | (2006.01) |
| *B82Y 15/00* | (2011.01) |

(Continued)

(52) U.S. Cl.
CPC ............... *G01N 27/447* (2013.01); *B82Y 5/00* (2013.01); *B82Y 15/00* (2013.01); *C12Q 1/6869* (2013.01); *G01N 27/44791* (2013.01); *G01N 33/48721* (2013.01); *G01N 33/68* (2013.01); *Y10S 977/852* (2013.01)

(58) Field of Classification Search
CPC ......... G01N 27/447; G01N 27/26; C12Q 1/00
See application file for complete search history.

(56) References Cited

U.S. PATENT DOCUMENTS

| | | | |
|---|---|---|---|
| 5,304,950 A | * | 4/1994 | Martin ................. H03F 3/08 250/214 A |
| 7,208,077 B1 | | 4/2007 | Albers et al. |

(Continued)

FOREIGN PATENT DOCUMENTS

| | | |
|---|---|---|
| CN | 101126735 A | 2/2008 |
| CN | 101194162 A | 6/2008 |

(Continued)

OTHER PUBLICATIONS

Yin et al. (IEEE, 2007).*

(Continued)

*Primary Examiner* — Jennifer Dieterle
(74) *Attorney, Agent, or Firm* — Baker Botts L.L.P.

(57) ABSTRACT

A system and method for detecting a single-molecule using an integrated circuit which includes at least one membrane having a nanopore located between first and second reservoirs and a low-noise preamplifier having an electrode formed on the surface thereof is provided. The method includes passing a target molecule through the nanopore, and measuring a current through the nanopore to detect the presence of a biomolecular entity, if any.

20 Claims, 21 Drawing Sheets

(51) Int. Cl.
*G01N 33/68* (2006.01)
*G01N 33/487* (2006.01)

(56) References Cited

U.S. PATENT DOCUMENTS

| | | | |
|---|---|---|---|
| 7,468,271 | B2 | 12/2008 | Golovchenko et al. |
| 7,491,628 | B2 | 2/2009 | Noca et al. |
| 7,635,423 | B2 | 12/2009 | Boussaad et al. |
| 2002/0006357 | A1 | 1/2002 | McGeoch et al. |
| 2004/0055901 | A1 | 3/2004 | Petersen et al. |
| 2005/0181383 | A1 | 8/2005 | Su et al. |
| 2005/0191495 | A1 | 9/2005 | Rueckes et al. |
| 2006/0078468 | A1 | 4/2006 | Gabriel et al. |
| 2006/0194263 | A1 | 8/2006 | Boussaad et al. |
| 2006/0240543 | A1 | 10/2006 | Folch et al. |
| 2006/0246497 | A1 | 11/2006 | Huang et al. |
| 2007/0292855 | A1 | 12/2007 | Dubin et al. |
| 2008/0035494 | A1 | 2/2008 | Gomez et al. |
| 2008/0094076 | A1 | 4/2008 | Hibbs et al. |
| 2008/0203380 | A1 | 8/2008 | Wang et al. |
| 2009/0142504 | A1 | 6/2009 | Ervin et al. |
| 2009/0173527 | A1 | 7/2009 | Benke et al. |
| 2009/0181381 | A1 | 7/2009 | Oldham et al. |
| 2009/0305319 | A1* | 12/2009 | Baudenbacher ... G01N 33/5005 435/29 |
| 2009/0325350 | A1 | 12/2009 | Radosavljevic et al. |
| 2010/0148126 | A1 | 6/2010 | Guan et al. |
| 2010/0285637 | A1 | 11/2010 | Khan et al. |
| 2010/0327874 | A1* | 12/2010 | Liu ............... G01N 33/48721 324/464 |
| 2010/0331194 | A1* | 12/2010 | Turner ............... C12Q 1/6869 506/2 |
| 2011/0057725 | A1 | 3/2011 | Ikeda et al. |
| 2011/0101996 | A1 | 5/2011 | Potyrailo et al. |
| 2011/0105870 | A1 | 5/2011 | Dale et al. |
| 2011/0220775 | A1* | 9/2011 | Triener ............. G01N 21/6428 250/201.1 |
| 2012/0025414 | A1 | 2/2012 | Schmidt et al. |
| 2012/0061239 | A1 | 3/2012 | Elibol et al. |
| 2012/0064519 | A1 | 3/2012 | Fang et al. |
| 2013/0180867 | A1 | 7/2013 | Rosenstein et al. |
| 2013/0285680 | A1 | 10/2013 | Sorgenfrei et al. |

FOREIGN PATENT DOCUMENTS

| | | |
|---|---|---|
| CN | 101346472 A | 1/2009 |
| WO | WO 2006/024023 A2 | 3/2006 |
| WO | WO 2007/075967 A2 | 7/2007 |
| WO | wo 2008/132643 * | 11/2008 |
| WO | WO 2009/046110 A1 | 4/2009 |
| WO | WO 2010/030057 A1 | 3/2010 |
| WO | WO 2011/123525 | 10/2011 |

OTHER PUBLICATIONS

International Search Report and Written opinion for PCT/US2012/020955, dated May 16, 2012.
International Search Report for PCT/US12/026292, dated May 29, 2012.
International Search Report and Written Opinion for PCT/US2013/031757, dated Jun. 4, 2013.
International Search Report and Written Opinion for PCT/US2013/031745, dated Jun. 4, 2013.
Suzuki, et al., "Microtechnologies for membrane protein studies", *Anal Bioanal Chem.*, 391(8):2695-2702 (2008).
CN Office Action dated Nov. 19, 2014 in CN Patent Application No. 201280004265.8.
Extended EP Search Report dated Dec. 15, 2014 in EP Application No. 12734088.
Besteman, K. et al., "Enzyme-coated carbon nanotubes as single molecule biosensors", Nano Letters, *American Chemical Society*, vol. 3, No. 6, Jan. 5, 2003, pp. 727-730, XP002982648.
Dongliang, Fu et al., "Label-free electrical detection of DNA hybridization using carbon nanotubes and graphene", *Nano Reviews*, vol. 1, No. 0, Aug. 31, 2010, XP055158479.
Hye-Mi, So et al., "Single-Walled Carbon Nanotube Biosensors Using Aptamers as Molecular Recognition Elements", *Journal of the American Chemical Society*, vol. 127, No. 34, Aug. 1, 2005, pp. 11906-11907, XP55032046.
Miron, Hazani et al., "Confocal Fluorescence Imaging of DNA-Functionalized Carbon Nanotubes", *Nano Letters*, vol. 3, No. 2, Feb. 1, 2003, pp. 153-155, XP055157827.
Sebastian, Sorgenfrei et al., "Label-free single-molecule detection of DNA-hybridization kinetics with a carbon nanotube field-effect transistor", *Nature Nanotechnology*, vol. 6, No. 2, Jan. 23, 2011, pp. 126-132, XP055157740.
Star, A. et al., "Label-free detection of DNA hybridization using carbon nanotube network field-effect transistors", *Proceedings of the National Academy of Sciences*, vol. 103, No. 4, Jan. 24, 2006, pp. 921-926, XP003023787.
U.S. Appl. No. 13/801,834, filed Mar. 13, 2013.
U.S. Appl. No. 13/942,242, filed Jul. 15, 2013.
U.S. Appl. No. 13/801,834, Jul. 28, 2015 Non-Final Office Action.
U.S. Appl. No. 13/942,242, Jul. 30, 2015 Notice of Abandonment.
U.S. Appl. No. 13/942,242, Jan. 22, 2015 Non-Final Office Action.
CN Office Action dated Jul. 10, 2015 in CN Patent Application No. 201280004265.8.

* cited by examiner

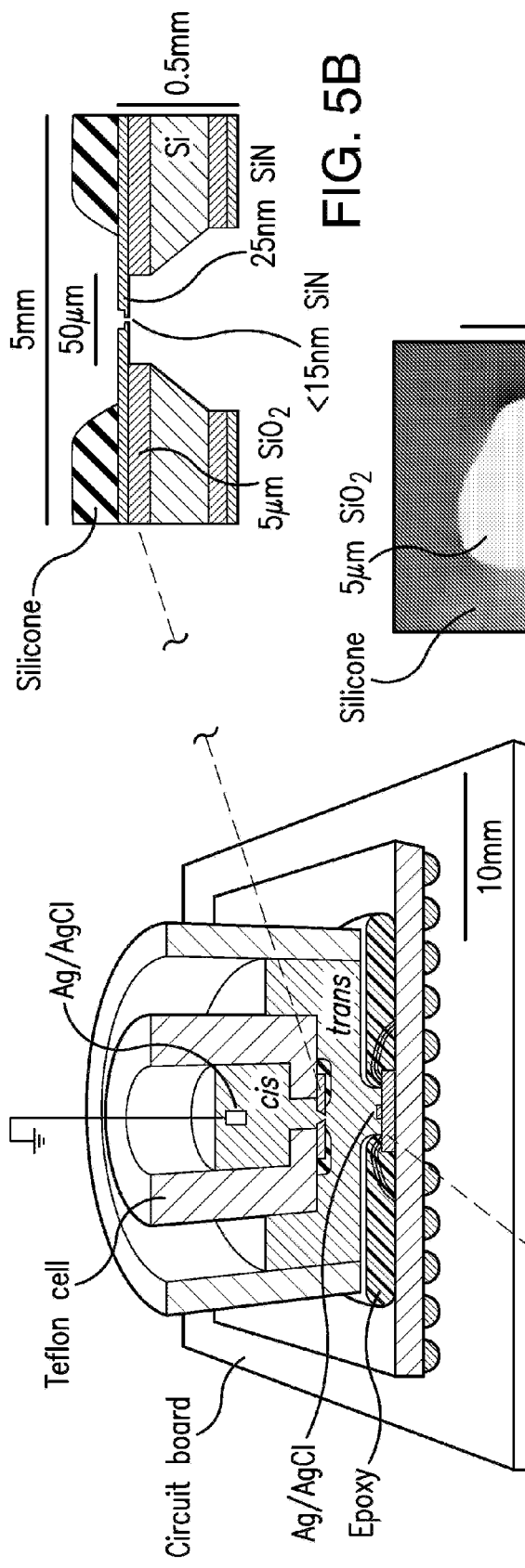
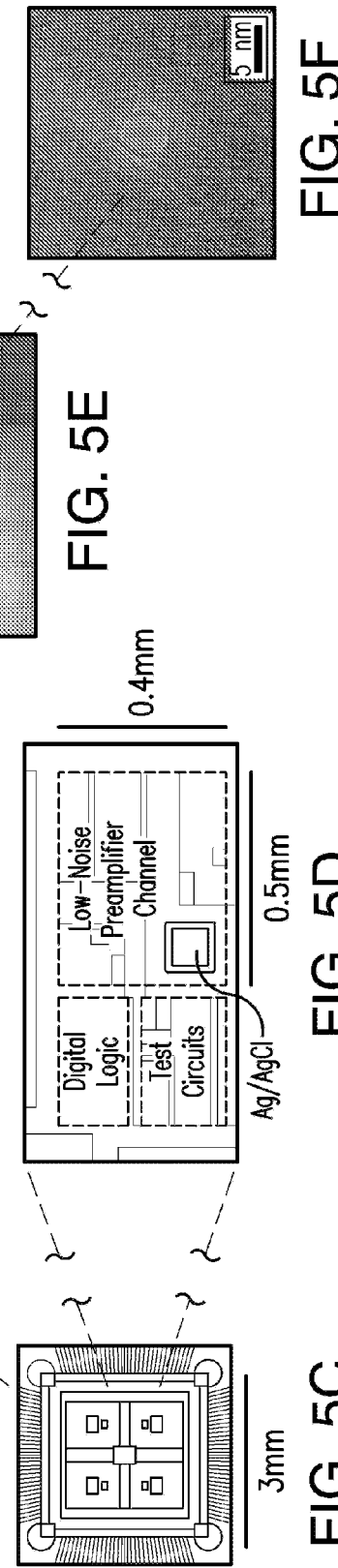

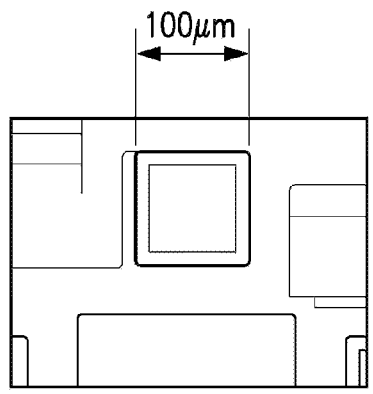
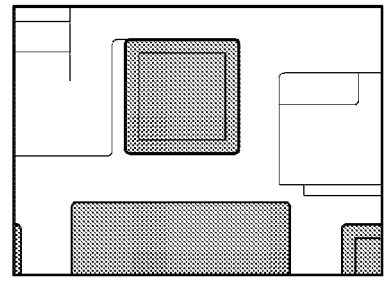
FIG. 8A  FIG. 8B
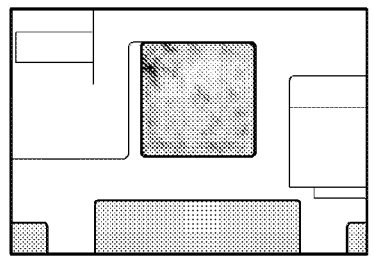
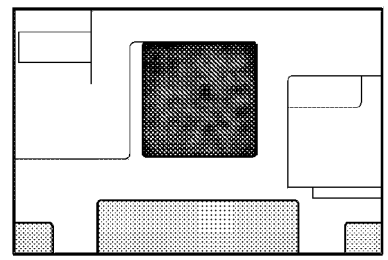
FIG. 8C  FIG. 8D
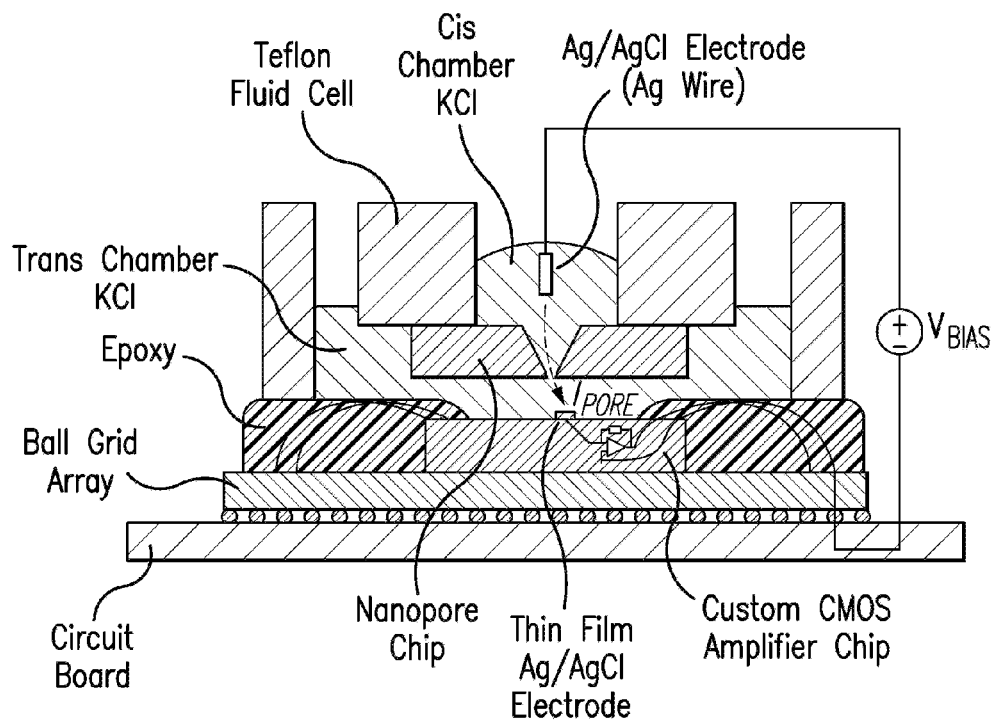
FIG. 9

Pre Bleach
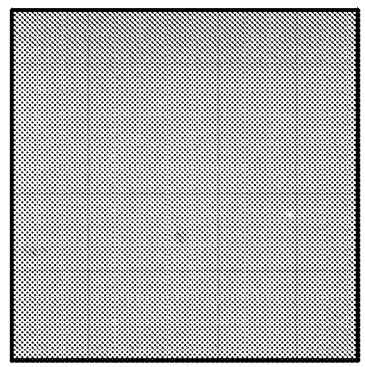
Post Bleach
(20 sec)
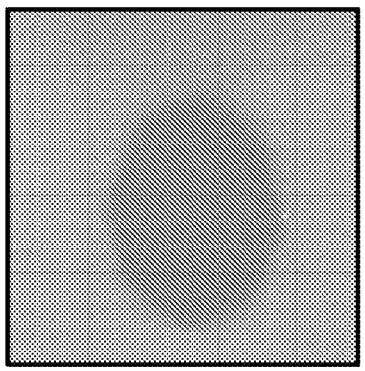
Post Bleach
(300 sec)
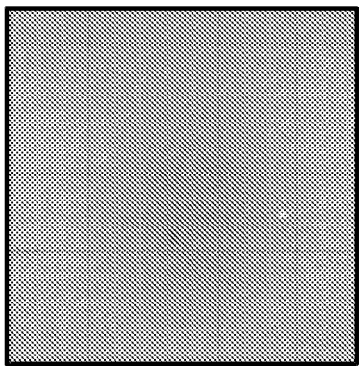
FIG. 20C

SYSTEMS AND METHODS FOR SINGLE-MOLECULE DETECTION USING NANOPORES

CROSS-REFERENCE TO RELATED APPLICATIONS

This application is a continuation of International Application No. PCT/US2012/026292, filed Feb. 23, 2012, which claims the benefit of U.S. Provisional Patent Application No. 61/445,918, filed Feb. 23, 2011, each of which is incorporated by reference herein in its entirety.

GRANT INFORMATION

This invention was made with government support under Grant No. CHE-0641523 awarded by National Science Foundation and HG006879 awarded by National Institute of Health. The government has certain rights in the invention.

BACKGROUND

The disclosed subject matter relates to the detection of single-molecules. There is demand for DNA sequencing systems to be single-molecule, massively parallel, and real-time. For single-molecule optical techniques, however, the signal from a single fluorophore can be <2500 photons/sec (equivalent to electrical current levels on the order of 50 fA). This can lead to complex optics to try to collect every photon emitted and makes scaling of the platforms difficult. Conversely, relevant chemical reactions can be intentionally slowed to 1 Hz (or slower) to allow sufficient imaging times for these weak, noisy optical signals.

In contrast, electrochemical detection approaches, can have significantly higher signal levels (often several orders of magnitude stronger), allowing for high-bandwidth detection with the appropriate co-design of transducer, detector, and amplifier. Nanopore technology is one potential bioelectronic transduction mechanism. Nanopores, however, can be limited by the relatively short time biomolecules spend in the charge-sensitive region of the pore. Restricted by the use of off-the-shelf electronics, the noise-limited bandwidth of nanopore measurements is typically less than 100 kHz, limiting the available sensing and actuation strategies and defying multiplexed integration which would be required for any sequencing application.

SUMMARY

Disclosed herein are new and improved systems and methods for single-molecule detection using nanopores.

The disclosed subject matter provides single-molecule detection and analysis based on the electrochemical conductance modulation of a solid-state or biological nanopore sensor including a low-noise multi-channel micro-scale preamplifier with integrated microelectrodes. In one embodiment, the nanopore sensor includes a low-noise multi-channel CMOS preamplifier with integrated microelectrodes.

In some embodiments, the microelectrodes can be on-die silver/silver-chloride (Ag/AgCl) microelectrodes. For example, a "two-chip" solution in which the pore and measurement electronics are on separate adjacent dice can be used, or a "one-chip" solution in which the pore is directly integrated on the substrate containing the measurement electronics can be used. In some embodiments, the surface of the preamplifier is exposed to one of the electrolyte reservoirs.

Monolithic integration of solid-state nanopores in an amplifier chip is also provided. Reduced parasitic capacitances (e.g., less than 1 pF) can be provided by integration of nanopores in silicon nitride membranes or graphene membranes onto the same chip as the measurement electronics, to provide more complete characterization of the high-frequency electronic properties of the nanopore.

In another embodiment, a method for detecting a single molecule using an integrated circuit which includes at least one membrane having a nanopore located between first and second reservoirs and a low-noise preamplifier having an electrode formed on the surface thereof is provided. The method includes passing a target molecule through the nanopore, and measuring a current through the nanopore to detect the presence of a biomolecular entity, if any.

In some embodiments, the preamplifier comprises a low-noise multi-channel CMOS preamplifier. The electrode can be created from a range of materials including Ag/AgCl, platinum, gold, and un-chlorinated silver.

In some embodiments, the nanopore is positioned on a silicon chip adjacent to the preamplifier. Alternatively, the nanopore comprises a nanopore directly integrated through the preamplifier. Is such an embodiment, the first and second reservoirs can be located on opposite sides of the preamplifier.

In some embodiments, the nanopore can comprise a solid state nanopore or a biological nanopore. The membrane can be a lipid bilayer. The integrated circuit can comprise a plurality of nanopores.

In some embodiments, the integrated circuit further comprises a ball grid array and a printed circuit board.

In another embodiment, an integrated circuit for single-molecule detection is provided. The integrated circuit comprises at least one membrane having a nanopore located between first and second reservoirs and a low-noise preamplifier for measuring the change in pore current upon passing a target entity through the nanopore. The preamplifier has at least one electrode formed on the surface thereof.

The accompanying drawings, which are incorporated and constitute part of this disclosure, illustrate certain embodiments of the disclosed subject mater and serve to explain its principles.

BRIEF DESCRIPTION OF THE DRAWINGS

Further features, the nature, and various advantages of the disclosed subject matter will be more apparent from the following detailed description of the embodiments and the accompanying drawings in which:

FIG. 5A-F is a graphical representation of the compact nanopore measurement platform in accordance with some embodiments of the disclosed subject matter;

FIGS. 8A, 8B, 8C, and 8D are images of the fabrication of on-chip electrodes in accordance with some embodiments of the disclosed subject matter;

FIG. 9 is a schematic of a two-chip stacked measurement cell in accordance with some embodiments of the disclosed subject matter;

FIG. 20A-C is a diagram of building lipid bilayers on the surface of a CMOS-integrated nanopore platform (CNP) design in accordance with some embodiments of the disclosed subject matter.

Figure 1:
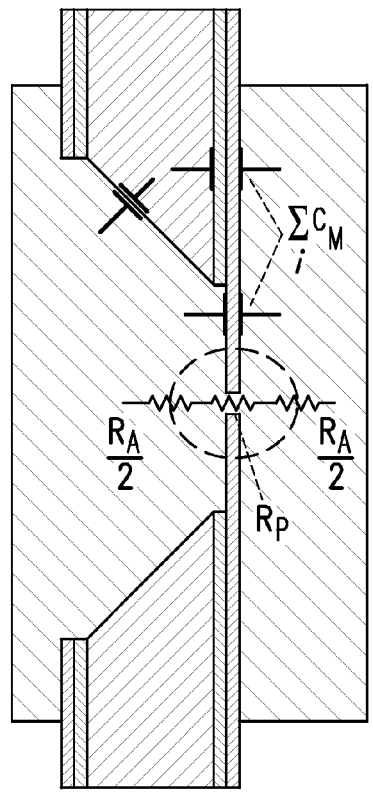
FIG. 1 is a graphical representation of the electronic impedances of a solid-state nanopore chip in accordance with some embodiments of the disclosed subject matter.

Throughout the drawings, the same reference numerals and characters, unless otherwise stated, are used to denote like features, elements, components or portions of the illustrated embodiments. Moreover, while the present disclosed subject matter will now be described in detail with reference to the Figures, it is done so in connection with the illustrative embodiments.

DETAILED DESCRIPTION

New and improved techniques are provided for single-molecule detection utilizing nanopore sensors. The present disclosure provides for significant reduction in input capacitance and improved noise performance, an improvement in the noise-limited bandwidth of the detection electronics for nanopores, a reduction in physical size, and increased throughput by utilizing parallelized nanopore measurements.

Nanopore sensors are single-molecule electrochemical systems in which two electrolyte reservoirs (i.e. aqueous salt buffers) are separated by a membrane containing a single nanoscale pore. Electrodes are placed in each of the reservoirs, and by establishing an electrical voltage gradient between the chambers, charged molecules can be induced to pass through the pore, with the presence of a molecule resulting in a transient change in the pore's electrochemical conductance. The measured electrical current corresponds to the transport of dissolved ions through the pore, and when a molecule, such as DNA, passes through the pore, there is a transient change in the ionic current. There are at least two attributes of this electronic sensor that give it single-molecule sensitivity. The first is the localized (nanoscale) geometry of charge sensitivity in the pore itself. The diameter d of a pore can be 1-10 nm, and due to electrolyte charge screening the measured current is highly insensitive to charge sources more than a few nanometers from the pore. The second attribute of nanopores is their high sensitivity, achieved by using high-mobility salt ions to infer the presence of a comparatively slow-moving biomolecule.

Analysis of bandwidth in nanopore sensing systems is similar to the analysis of voltage-clamp electrophysiology recordings, except that the magnitudes of contributing elements can vary significantly. Because these systems produce weak transient signals, their useful signal bandwidths are generally constrained not by small-signal frequency response but by the signal-to-noise ratio (SNR). Detailed treatments of noise in ion channel recordings often address scenarios with signal amplitudes of 10 pA or less, for which relevant bandwidths are typically less than 10 kHz. However, nanopore sensors often use more concentrated electrolytes and higher holding potentials, producing current pulses of 100 pA from alpha-Hemolysin, 300 pA for MspA, and upwards of 4 nA for solid-state nanopores.

Figure 2:
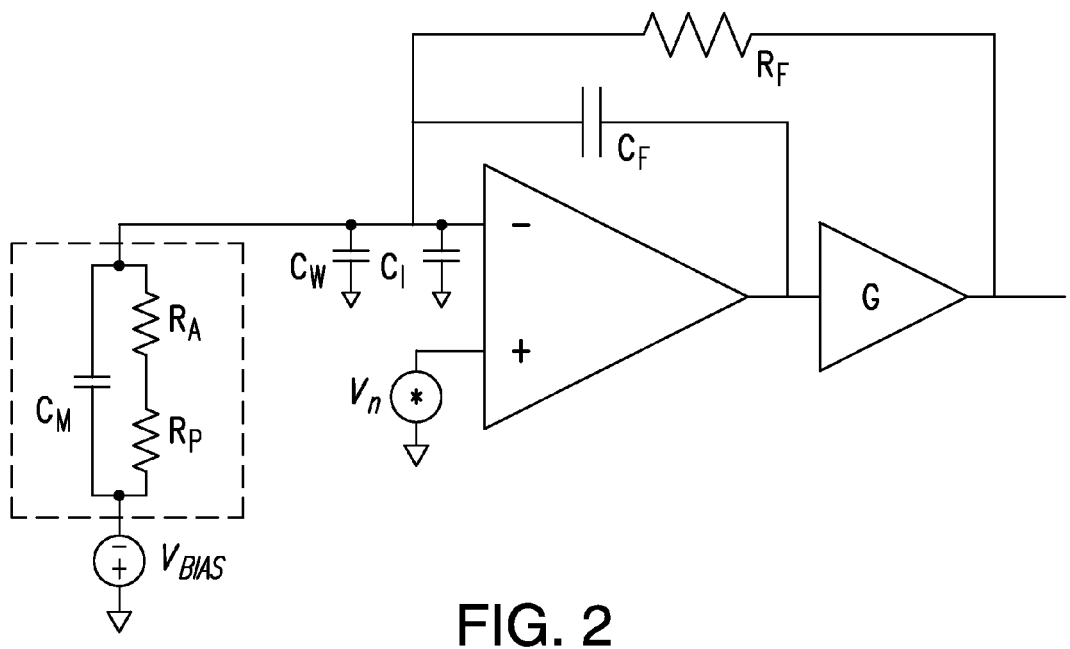
FIG. 2 is a electrical model of a voltage-clamp current premaplifier in accordance with some embodiments of the disclosed subject matter.

A nanopore can be modeled as an ionic resistance $R_P$ in series with an access resistance $R_A$, along with a shunt capacitance $C_M$ from the supporting membrane structure, as shown in FIG. 1. In addition, capacitance is associated with the electrode wiring ($C_W$), the amplifier input stage ($C_I$), and the amplifier feedback elements ($C_{FB}$). An electrical circuit equivalent of this arrangement is shown in FIG. 2.

Figure 3:
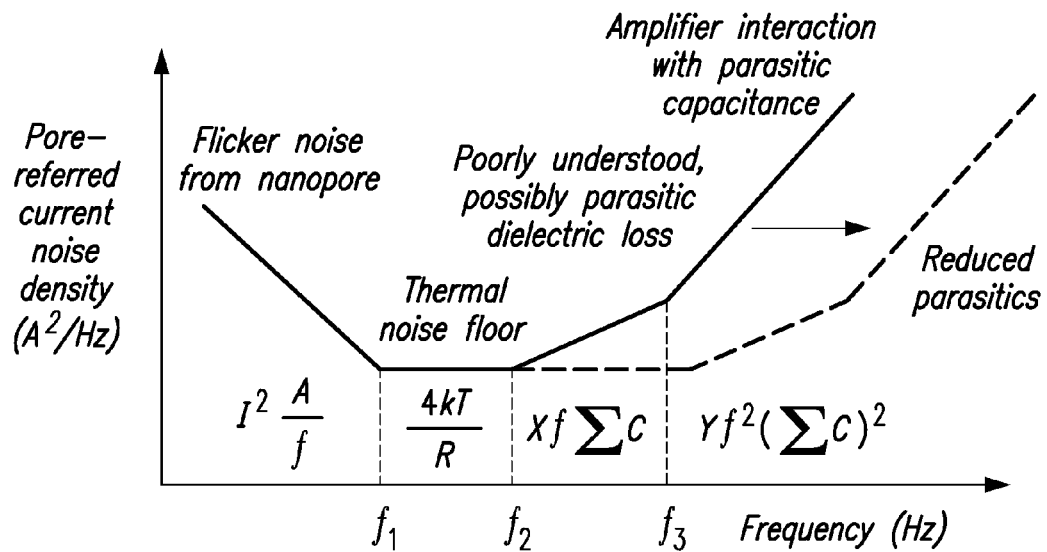
FIG. 3 is a graph of the typical spectral density of nanopore measurement noise in accordance with some embodiments of the disclosed subject matter.

The noise spectrum of nanopore current measurements has several distinct regions, as illustrated in FIG. 3 for the purpose of illustration. At low frequencies (<100 Hz), 1/f noise and Johnson noise from the pore conductance is present. At moderate frequencies (100 Hz-10 kHz) sources of white noise in the pore or measurement electronics can appear, along with thermal noise generated by lossy dielectric materials (FIG. 3). At higher frequencies (>10 kHz), the dominant noise source is the interaction between the amplifier's voltage noise with the total capacitance present at the input node. In this regime the input-referred noise spectral density scales with $i_n^2 \approx (2\pi f C)^2 * e_n$, where $e_n$ is the equivalent input voltage noise power of the amplifier. The value C is the sum of several distinct physical capacitances: the thin membrane in which the nanopore is fabricated acts as a capacitor between the first and second (i.e. cis and trans) reservoirs; stray capacitances can be present in any wiring between the electrodes and the amplifier; and the amplifier itself will have a characteristic capacitance at its input. The membrane capacitance can be the largest of these three elements, contributing as much as several hundred picofarads. However, that noise can be significantly reduced by limiting the fluid contact area with the chip, or by passivating the surface of the chip with a thick dielectric. As the membrane capacitance ($C_{MEMBRANE}$) reduces, the attention turns to the reactance of the electrode wiring and amplifier input. Certain known electrophysiology amplifiers typically have an input capacitance ($C_{IN}$) on the order of 15 pF, and a wiring capacitance ($C_{WIRING}$) of several picofarads is not unreasonable, which can limit the abilities of the nanopore sensor.

In further detail, the input-referred power spectral density is:

$$S_n^2(f) \approx [2\pi f(C_M + C_W + C_I + C_{FB})v_n]^2 \quad (1)$$

and root-mean-squared noise is given by:

$$I_{RMS}(B) \approx \frac{2\pi}{\sqrt{3}} B^{\frac{3}{2}} (C_M + C_W + C_I + C_{FB}) v_n \quad (2)$$

where $v_n$ is the voltage noise density (V/√Hz) of the input amplifier and B is the measurement bandwidth.

Figure 4:
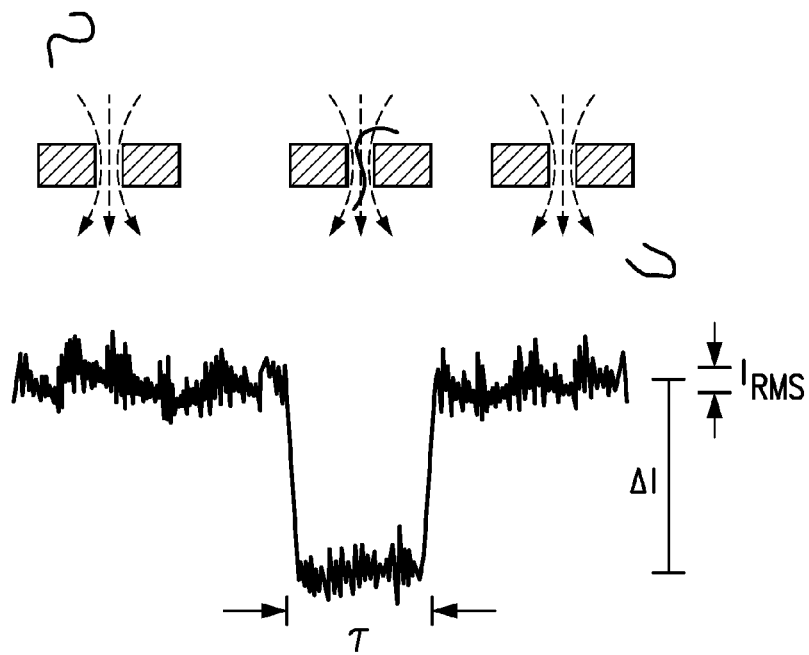
FIG. 4 is a illustration of the types of current pulses which result from single-molecule interactions with nanopores in accordance with some embodiments of the disclosed subject matter.

For purposes of arriving at a signal-to-noise (SNR) metric, previously the signal level has been defined as ΔI, the average change in current caused by the presence of a molecule in the pore. The corresponding SNR, which is a function of the measurement bandwidth, is given by $\Delta I/I_{RMS}(B)$. While this is a useful expression, it neglects the fact that the signals themselves are also filtered by the choice of measurement bandwidth. To more accurately evaluate performance when the signal content exceeds the available bandwidth, the SNR is instead defined as:

$$SNR(B, \tau) = \frac{\Delta I}{I_{RMS}(B)} \frac{1}{\sqrt{1 + \frac{1}{2B\tau}}} \quad (3)$$

where τ is the minimum duration of the signals of interest as shown in FIG. 4 for the purpose of illustration. A consequence of this modification is that the SNR does not necessarily decrease with measurement bandwidth. If a signal contains brief transient events, SNR can increase for wider bandwidths despite higher $I_{RMS}$ values.

Combining these expressions, the maximum bandwidth ($B_{MAX}$) which maintains an acceptable signal-to-noise ratio ($SNR_{MIN}$) can be defined. If τ<100 μs and B>>½τ, this upper bound on the measurement bandwidth is given by:

$$B_{MAX} \approx \left[ \frac{\Delta I \sqrt{3}}{SNR_{MIN} \times 2\pi (C_M + C_W + C_I + C_{FB}) v_n} \right]^{\frac{2}{3}} \quad (4)$$

It is clear that the available bandwidth $B_{MAX}$ increases for larger signal levels (ΔI) and decreases for larger capacitances and amplifier voltage noise. All of the capacitances in this expression are extrinsic to the nanopore and therefore, eligible for improvement without affecting the properties of the pore itself.

In accordance with one aspect of the disclosed subject matter, a CMOS-integrated nanopore platform (CNP) is based around a low-noise current preamplifier and a high-performance solid-state nanopore or a biological nanopore (as described further below). The preamplifier circuitry can occupy 0.2 mm² in a 0.13 μm mixed-signal CMOS process and is positioned directly within the fluid chamber, as shown in FIG. 5. In one embodiment, a thin silicon nitride nanopore, designed with high conductivity and low capacitance, is placed into the fluid chamber above the amplifier, as described below in more detail. The resulting platform allows for improved high-frequency noise performance over traditional measurements which rely on external electrophysiology amplifiers such as the Axopatch 200B (available from Molecular Devices Inc.) or EPC-10 (available from HEKA Electronik GmbH). The CNP's planar amplifier design is also well suited to parallelization, and with the addition of fluidics to isolate the trans chambers of an array of nanopores, multi-channel detection can be supported by the platform (as described in detail below).

While described herein with respect to CMOS integrated circuit technology for the purpose of illustration and not limitation, the disclosed subject matter can be used with any integrated circuit technology, such as but not limited to CMOS, bipolar, SiGE, any node, and any other suitable integrated circuit technology known to one of ordinary skill in the art.

Figure 6A:
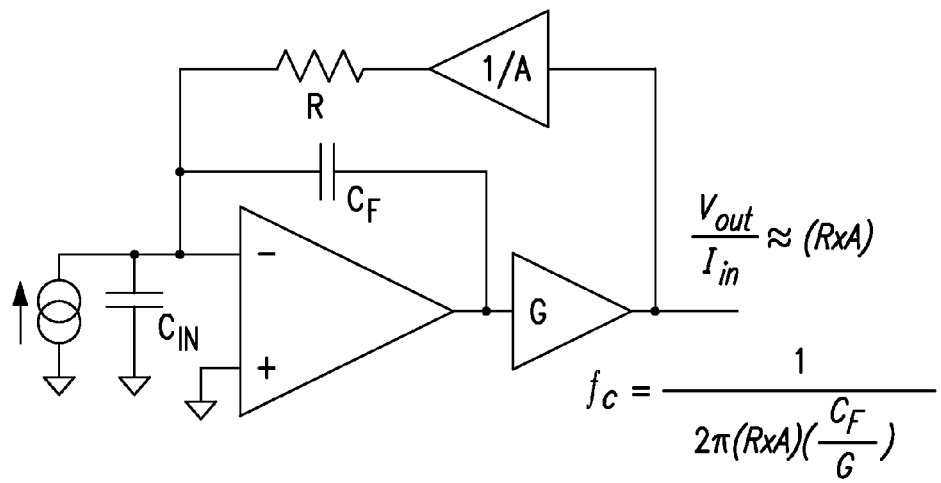
FIGS. 6A and 6B are schematics of the preamplifier circuit topology in accordance with some embodiments of the disclosed subject matter.
Figure 6B:
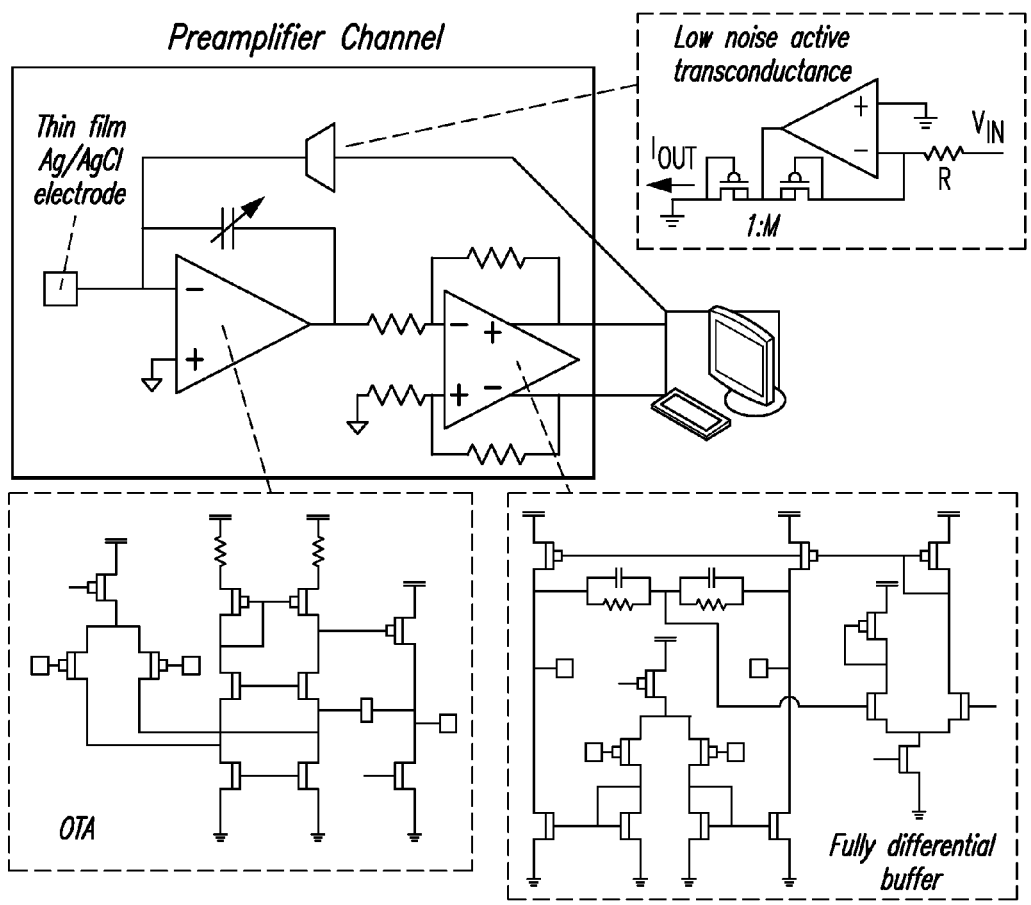

In one embodiment, a chip hosts a multi-channel preamplifier, such as an 8-channel preamplifier with the topology shown in FIG. 6a (and the detailed circuit description of FIG. 6b) for the purpose of illustration. Each channel consists of a charge-sensitive preamplifier along with a low-noise transconductance to pass any DC current. A programmable active negative capacitance is also included, which can extend the bandwidth but does not decrease the input-referred noise. The transconductor is wired in a feedback loop which is tuned such that the overall transimpedance gain has a similar first-order response to a classical resistive-feedback stage with a gain of 100 MΩ. The attenuator '1/A' is designed as a filter with constant attenuation at signal frequencies but high gain at very low frequencies so that it suppresses DC offsets at the output, improving dynamic range. The frequency response can be tuned by adjusting the loop gain through the gain stage G. Similar to classical high-gain transimpedance amplifiers, the overall response cannot be extended to arbitrarily high frequencies for stability reasons, and a simple filter stage (not shown) is cascaded with the amplifier output to restore its flat frequency response before being digitized. The value of $C_F$ is programmable as 1 pF, 100 fF, or 50 fF, and the gain-bandwidth product of the OTA is 100 MHz. The total input capacitance of each channel is 1 pF+$C_F$.

The chip can have any other circuitry in addition to the preamplifier. For example but not limitation, the chip can include data converters, digital signal processing, logic, memory, and/or any other suitable circuitry known to one of ordinary skill in the art.

Figure 7:
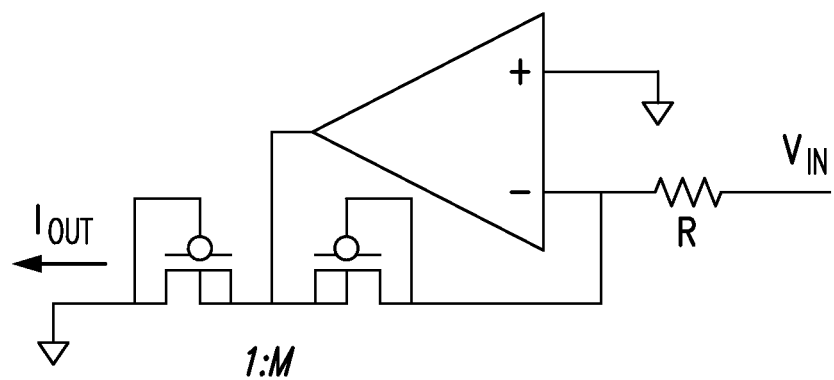
FIG. 7 is a circuit design of the low-noise current source which substitutes for a feedback resistance in accordance with some embodiments of the disclosed subject matter.

The 3×3 mm die can be produced in a standard 0.13 μm 1.5V mixed-signal process, with each preamplifier occupying approximately 0.3 mm² and consuming 5 mW. Alternatively, the eight low-noise transimpedance amplifiers each occupy 0.2 mm² and implement the circuit topology of FIG. 2. While some of the results presented herein utilize only one channel, however, the channels are independent and can be operated in parallel for continuous measurements of eight or more devices if appropriate fluidics are implemented as described below. Furthermore, any suitable number of channels can be used. Several elements of a classical transimpedance topology are adapted to make the design suitable for modern integrated circuit technology. In particular, it is necessary to achieve a well-defined high transimpedance gain without the availability of high-value resistances. Purely capacitive feedback would be appropriate if not for the significant DC bias currents of nanopore sensors. Thus in place of a traditional feedback resistor, the CNP implements a DC servo loop with an active low-noise current source, producing a closed-loop circuit with a transimpedance gain of 100 MΩ as shown in FIG. 7. A digitally selectable feedback capacitor $C_F$ and the gain element G maintain loop stability by reducing the closed-loop gain above 30 kHz, and the preamplifier is followed by a filter to restore a flat gain response to >1 MHz. The input stage is designed for negligible gate leakage and a gate capacitance below 1 pF. When operated with $C_F$=0.15 pF, the preamplifier has a total input capacitance of $C_T$=1.3 pF, voltage noise $v_n$=5 ηV/√Hz, and consumes 5 mW from a 1.5V supply.

The preamplifier and fluid cell can be located on a 15-cm-by-13-cm printed circuit board along with power regulation, biasing, and analog signal paths. The board is powered by four AAA batteries and draws a total of 30 mA, allowing a full day of continuous operation. Digital control interfaces are galvanically isolated, and signal outputs are fully differential. A second circuit board contains a four-pole Bessel antialiasing filter as well as analog-to-digital converters and a high-speed USB interface.

In accordance with one aspect of the disclosed subject matter, thin-film electrodes (e.g. Ag/AgCl) are fabricated on the surface of the amplifier chip to enable a direct electrochemical interface between the preamplifier and the electrolyte. With integrated amplifiers of sub-millimeter dimensions, macro-scale electrodes can limit the density. Thus, fabrication on the surface of the chip in accordance with the disclosed subject matter provides for small size and increased scalability of the design. In accordance with a preferred embodiment, the electrode can be an Ag/AgCl microelectrode, which provides high performance voltage-clamp measurements. However, additional electrodes that can be used include, but are not limited to, platinum, gold, un-chlorinated silver, and other suitable electrodes known to one of ordinary skill in the art.

For example, in the exemplary 0.13 μm process used to fabricate the die the top exposed metal is aluminum, which is unsuitable for chemical environments. The aluminum is chemically etched away in phosphoric acid, exposing the adhesion and diffusion barrier layers beneath. Several microns of silver can be deposited electrochemically from a plating solution containing aqueous potassium silver cyanide (commercially available from Transene, Danvers, Mass.). The surface is then treated with ferric chloride to create a silver chloride coating on the electrode. Images of this fabrication sequence are shown in FIG. 8 for the purpose of illustration. FIG. 8a shows the electrode as received from the foundry. FIG. 8b shows the exposed aluminum is chemically etched away. FIG. 8c shows several micros of silver are deposited electrochemically. FIG. 8d shows the silver chlorinated with $FeCl_3$ to create an Ag/AgCl microelectrode. This process yields electrodes which are stable operating with nanoampere-scale currents for several hours.

In accordance with some embodiments of the disclosed subject matter, a two-chip stacked measurement cell is provided. The custom measurement cell allows discrete nanopore chips to be interfaced to the integrated preamplifier having an electrochemically active surface electrode. As illustrated in FIG. 9 for the purpose of illustration, a discrete nanopore chip can be mounted in a Teflon fluid cell using KWIK-CAST silicone adhesive (commercially available from World Precision Instruments, Sarasota, Fla.), and positioned immediately above the amplifier.

In this cell the trans reservoir is in direct contact with the amplifier's microelectrode, while a separate chlorinated silver wire serves as the cis electrode. Note that in contrast with the amplifier input node, since this counterelectrode is only providing a DC voltage bias it is not significantly affected by any wiring parasitics.

Figure 10:
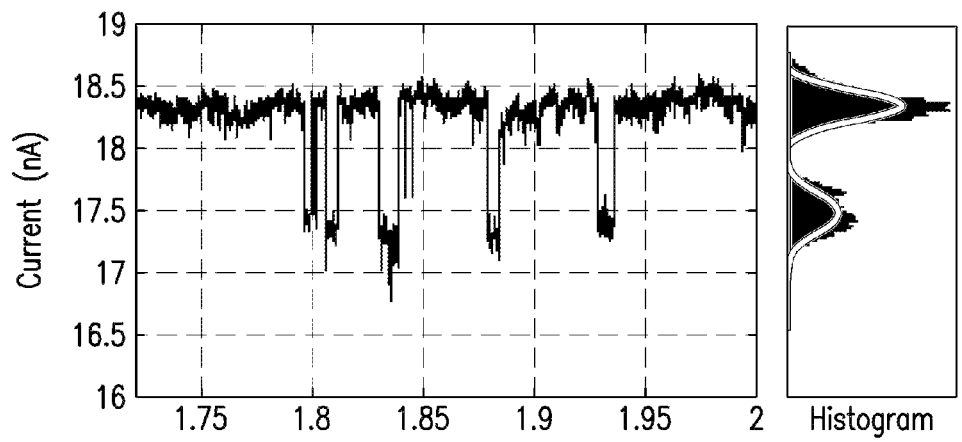
FIG. 10 is graph of the transient measurements of DNA molecules passing through a nanopore in accordance with some embodiments of the disclosed subject matter.

In accordance with one aspect of the disclosed subject matter, DNA translocation events were measured in the two-chip configuration to demonstrate the amplifiers and integrated Ag/AgCl electrodes. Measurements were performed at a bias of 300 mV in a potassium chloride buffer (e.g., 1M KCl, 1 mM EDTA, pH 8.0). Lambda DNA (commercially available from New England BioLabs, Ipswich, Mass.) was added to the cis chamber, and the resulting current traces show an appropriate characteristic two-state transient response, as shown in FIG. 10 for the purpose of illustration.

Figure 11:
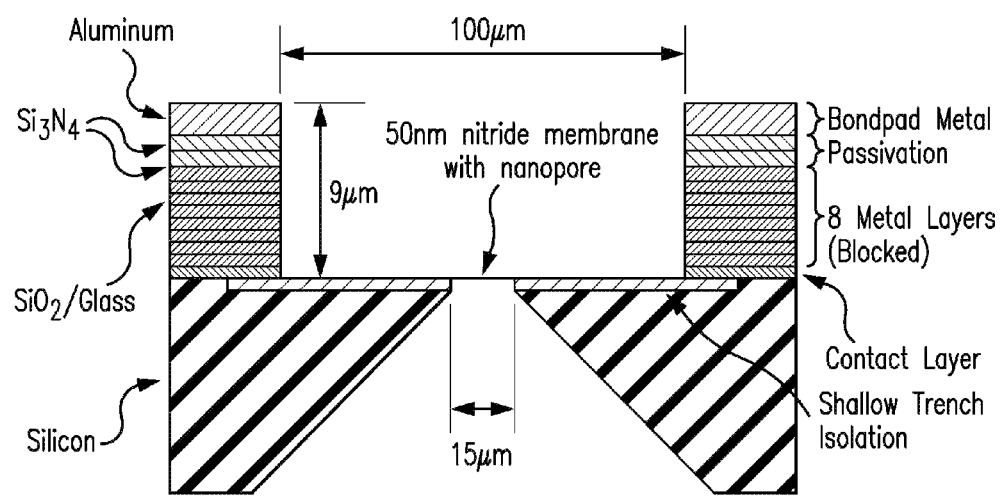
FIG. 11 is a local cross section schematic of a post-fabricated silicon nitride membrane in accordance with some embodiments of the disclosed subject matter.
Figure 12:
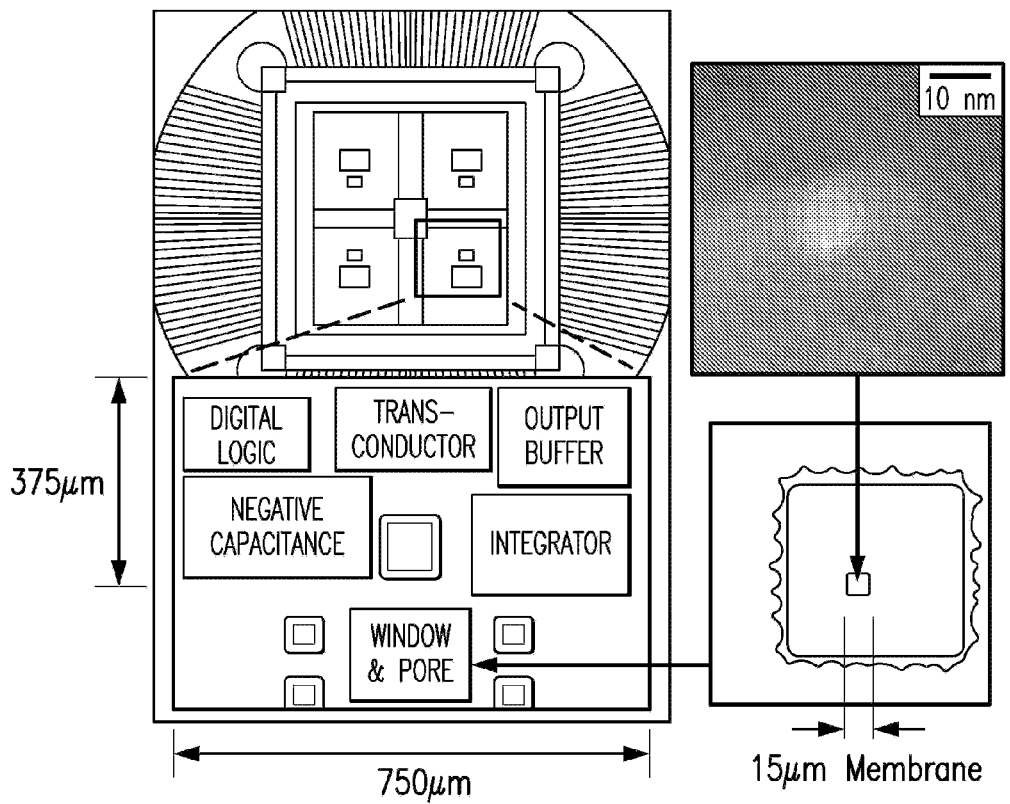
FIG. 12 is a series of die photographs showing an integrated nanopore in accordance with some embodiments of the disclosed subject matter.

In accordance with some embodiments of the disclosed subject matter, a single-chip nanopore and preamplifier chip integration and a process for post-fabricating solid-state nanopores into the preamplifier chip are provided. For example, during the design of the chip several 200×200 μm areas can be reserved for later fabrication of suspended dielectric windows. In these areas of the chip, the metal routing layers are blocked, resulting in a thick stack of approximately 8 μm of alternating glass fill and silicon nitride capping layers. The majority of the dielectric stack is etched from the front side using an inductively-coupled $CHF_3+O_2$ or $SF_6$ plasma, using evaporated chromium as a mask. After depositing and patterning a PECVD $Si_3N_4$ mask on the back of the die, the chip is mounted in a custom PDMS cell to protect the front side features, and localized openings in the silicon substrate are etched anisotropically in heated 30% wt KOH. A short dip in buffered hydrofluoric acid is then used to isolate a single 50 nm layer of silicon nitride from the original dielectric stack as a suspended membrane. Finally, nanopores are drilled through these nitride membranes with a high resolution transmission electron microscope. A cross-section of the final window structure is illustrated in FIG. 11, and a TEM image of one of these nanopores (having a thickness of about 6 nm in diameter) can be seen in FIG. 12. The design allows for the integration of four solid-state nanopores per chip with the electronics surrounding each pore as shown in the die photo of FIG. 12. However, more than four nanopores can be integrated on a single die the same size by reducing the footprint for the pore electronics.

Figure 13:
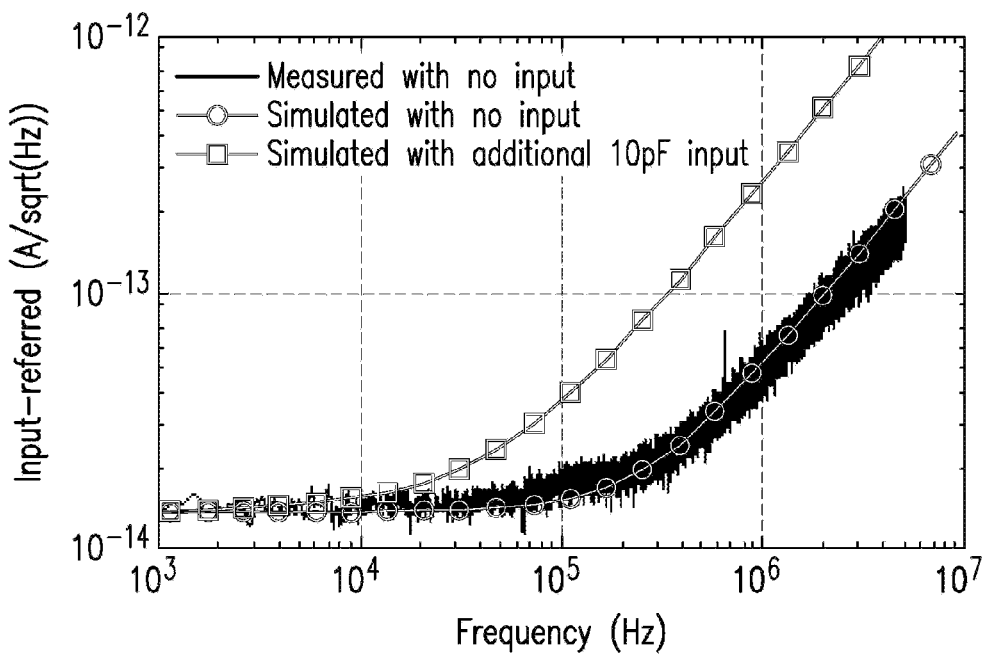
FIG. 13 is a graph of the measured and simulated input-referred noise in accordance with some embodiments of the disclosed subject matter.

With no external input, the amplifiers show a measured input-referred noise in good agreement with simulations, as shown in FIG. 13 for the purpose of illustration. Noise spectral density at low frequencies is approximately 12 fA/√Hz, comparable to a 110 MΩ resistor. At frequencies above 10 kHz, the noise is very sensitive to input capacitance, as expected.

Figure 14:
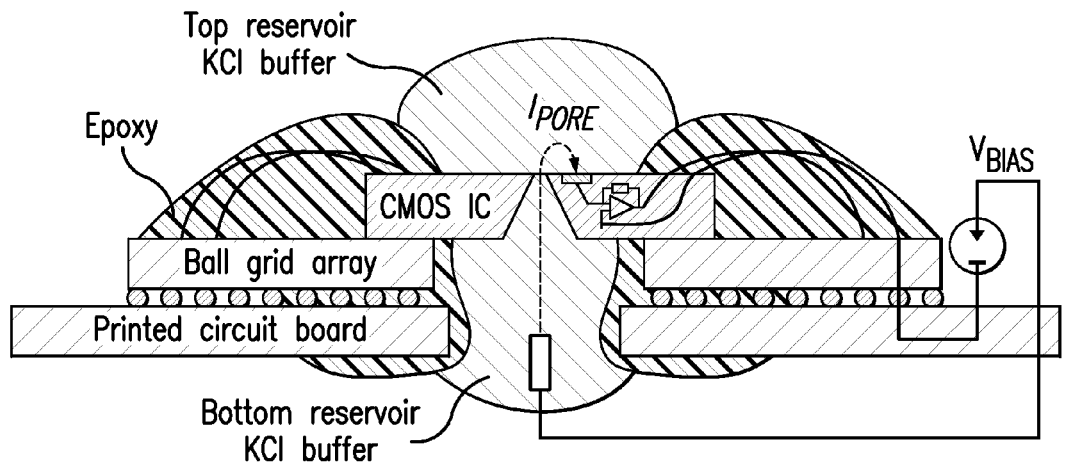
FIG. 14 is diagram of a single-chip packaging in accordance with some embodiments of the disclosed subject matter.
Figure 15:
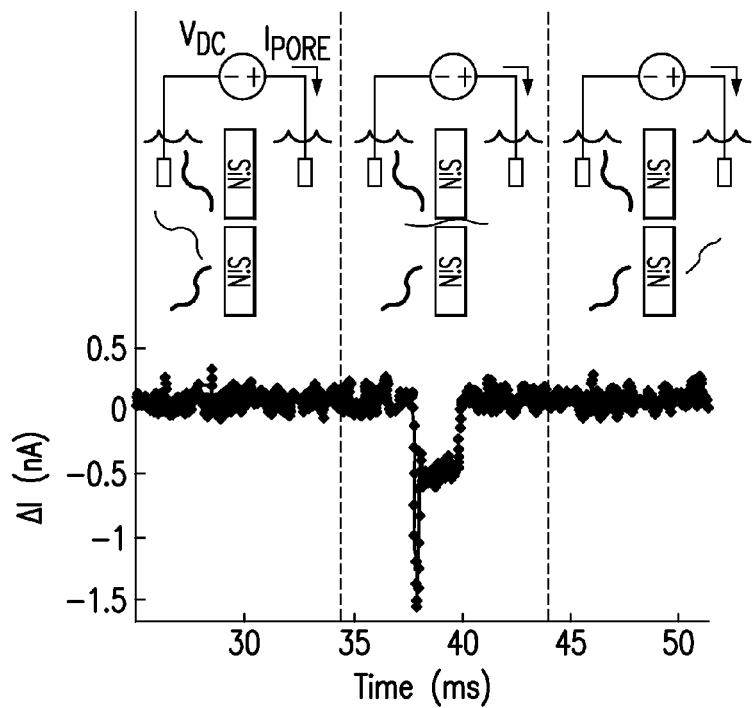
FIG. 15 is graph of DNA translocation through a nanopore sensor in accordance with some embodiments of the disclosed subject matter.

In accordance with some embodiments, a packaging of the single-chip post-processed integrated circuit to support electrolyte reservoirs on either side of the chip is provided, as shown in FIG. 14 for the purpose of illustration. To isolate the potential at which the circuits operate from the electrolyte bias voltage, the circuits are implemented with triple-well isolation. As part of post-processing, a backside insulating passivation layer is provided to prevent any electrochemical interactions between the substrate and the solution. This setup was used to perform wet electrical measurements using external Ag/AgCl electrodes. For the purpose of illustration, FIG. 15 shows the results of DNA translocation experiments with 1M KCl and 20 ng/μL 15 kbp dsDNA at 100 mV bias.

In accordance with some embodiments of the single chip embodiment, the "top" Ag/AgCl electrode is integrated on the die by electroplating Ag onto existing metal pads on the CMOS chip (as shown in FIG. 14). To drive $C_{MEMBRANE}$ below 1 pF, access of the electrolyte to the chip can be reduced to 250-μm-by-250-μm, combined with a 15-μm-by-15-μm nitride window. The presence of back-end interconnect layers in the chip provides a dielectric stack 8-μm thick (FIG. 11), yielding a capacitance of only 4.4 pF/mm². The membranes in the vicinity of the pore can be thinned to be less than 10 nm, further improving signal levels. These ultra-thin membranes will help to improve the spatial resolution of nanopore devices, combined with the fast temporal resolution uniquely enabled by the integrated electronics. As shown in FIG. 14, the chip packaging also includes a ball-grid-array package and printed-circuit board to accommodate the wet environment. Of note, using an external electrode for the "bottom" Ag/AgCl electrode does not degrade the noise-limited bandwidth for detection since only capacitances on the amplifier side of the pore shape the noise.

Figure 16:
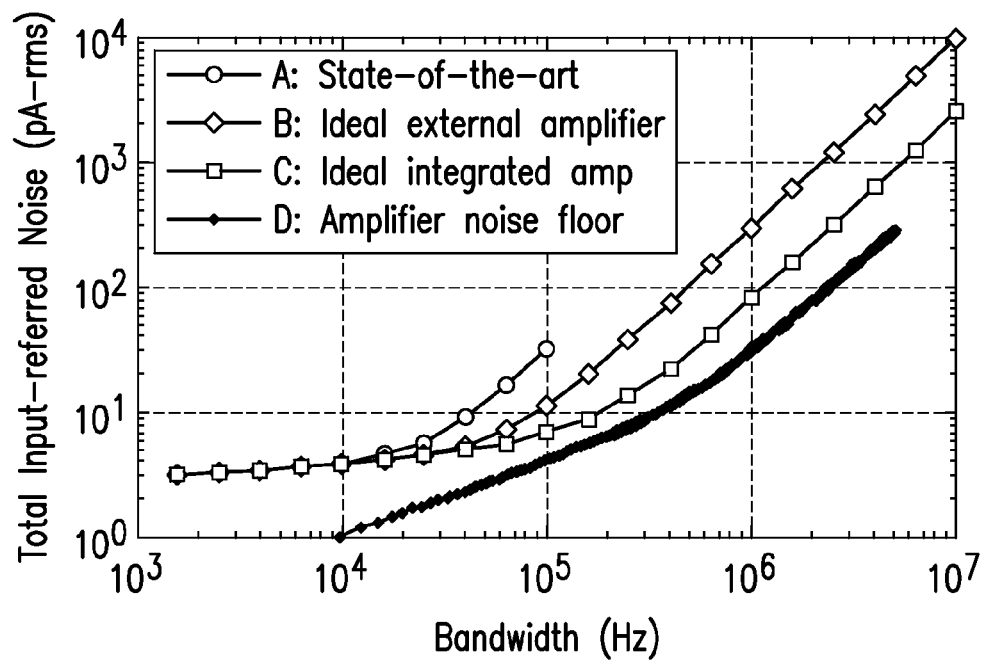
FIG. 16 is graph of the nanopore input-referred noise verses measurement bandwidth in accordance with some embodiments of the disclosed subject matter.

For the purpose of illustration and not limitation, FIG. 16 is a plot of the total RMS current noise that can be expected in several scenarios. The tolerable noise level depends on the signal being measured, but for reasonable solid-state nanopore sensing scenarios the noise-limited bandwidth can be defined as the bandwidth at which the noise is larger than 100 $pA_{rms}$. Scenario A approximates the current state-of-the-art for solid-state nanopores, as measured by a discrete amplifier with $C_{IN}$=15 pF, $C_{WIRING}$=10 pF, and $C_{MEMBRANE}$=60 pF. For example, the Axopatch 200B patch clamp amplifier (Molecular Devices, Sunnyvale, Calif.) is a low-noise instrument which has been improved for electrophysiology applications that have similar constraints as nanopore sensors. However, as discussed previously, at frequencies above approximately 10 kHz the primary factor determining the amplifier noise density is the total input capacitance. On this metric, a discrete amplifier cannot compete with an integrated solution. Additionally, an immediate practical concern is that the Axopatch does not support signal frequencies higher than 100 kHz. Scenario B estimates the lowest noise that could likely be achieved with a discrete amplifier by reducing $C_{MEMBRANE}$ to 1 pF while $C_{IN}$ and $C_{WIRING}$ remain the same. While this represents a several-fold improvement over today's state of the art, the useful bandwidth is still constrained by wiring and amplifier parasitics. Scenario C simulates the additional benefit of using an integrated amplifier with $C_{IN}$=1 pF and $C_{WIRING}$=0. Trace D plots the measured input noise floor of a preamplifier in accordance with the disclosed subject matter with no pore connected ($C_{MEMBRANE}$=$C_{WIRING}$=0). As can be seen, an integrated solution using a preamplifier in accordance with the disclose subject matter is superior to methods using known amplifiers.

Figure 17:
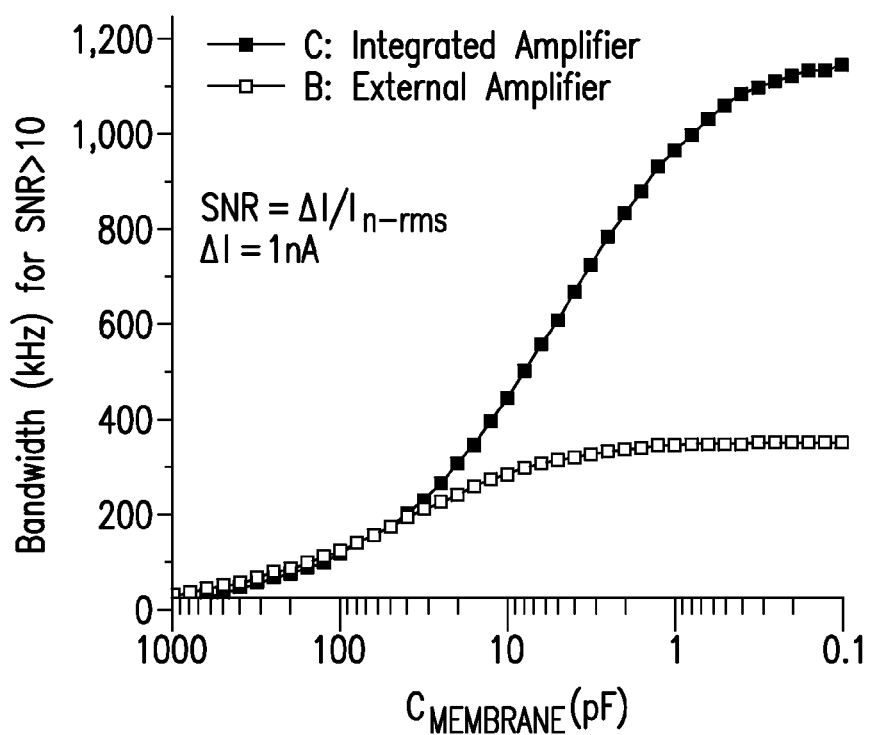
FIG. 17 is graph of the noise-limited bandwidth in accordance with some embodiments of the disclosed subject matter.

For the purpose of illustration and not limitation, FIG. 17 shows the noise-limited bandwidth for a signal level of 1 nA, comparing measurement with the Axopatch to measurement with the integrated amplifier in accordance with the disclosed subject matter as a function of $C_{MEMBRANE}$. For $C_{MEMBRANE}$<1 pF, bandwidths in excess of 1 MHz can be achieved for integrated amplifiers in accordance with the disclose subject matter.

Nanopore signal fidelity is extremely sensitive to parasitic electronic elements at the amplifier input, including any capacitance arising from the pore membrane (FIG. 1). Silicon nitride nanopores are fabricated in thin suspended dielectric windows on silicon substrates, and $C_M$ can be modeled as a parallel-plate capacitance of the constituent elements of $C_M$=$\Sigma_i \epsilon_0 \epsilon_r A_i/d_i$, where $\epsilon$ is the permittivity of free space, $\epsilon_r$ is the relative permittivity of the dielectric, $A_i$ is the area of fluid contact with the membrane substrate, and $d_i$ is the thickness of the dielectric. Early solid-state nanopores had values of $C_M$ larger than 300 pF. For the nanopores utilized in accordance with the disclosed subject matter (FIG. 5), a 50×50 μm suspended 25 nm silicon nitride window is supported by a 5 μm thermal $SiO_2$ layer which significantly reduces $C_M$. Additionally, in the course of mounting the nanopore to the fluid cell, the surface of the membrane chip is covered with a silicone elastomer, leaving only a minimal area exposed to the electrolyte. As a result, $C_M$ is reduced to less than 6 pF for nanopores in accordance with the disclosed subject matter (FIG. 5). With further fabrication efforts, $C_M$ can be reduced below 0.5 pF.

The close integration of the measurement electronics also reduces wiring capacitance ($C_W$). In platforms with external amplifiers, $C_W$ results from any capacitive coupling to other nodes (typically greater than 2 pF) from the short length (<10 cm) of wire which connects one Ag/AgCl electrode to the amplifier input. The use of unshielded wires (chosen to reduce parasitic capacitance) necessitates performing measurements in a Faraday cage to reduce electromagnetic interference. In the CNP design, the distance between an Ag/AgCl surface electrode and the amplifier input can be less than 100 μm and there are minimal requirements for external shielding. The presence of the electronic circuitry immediately adjacent to the fluid chamber, however, means that the ions in the electrolyte can capacitively couple to the metal wiring of the integrated circuits. To minimize this effect, the surface of the amplifier chip is covered with 200 μm-thick SU-8 in all areas outside the electrode. This augments the 6 μm of passivation dielectric present by default on the chip surface. The resulting $C_W$ is less than 1 pF.

Figure 18:
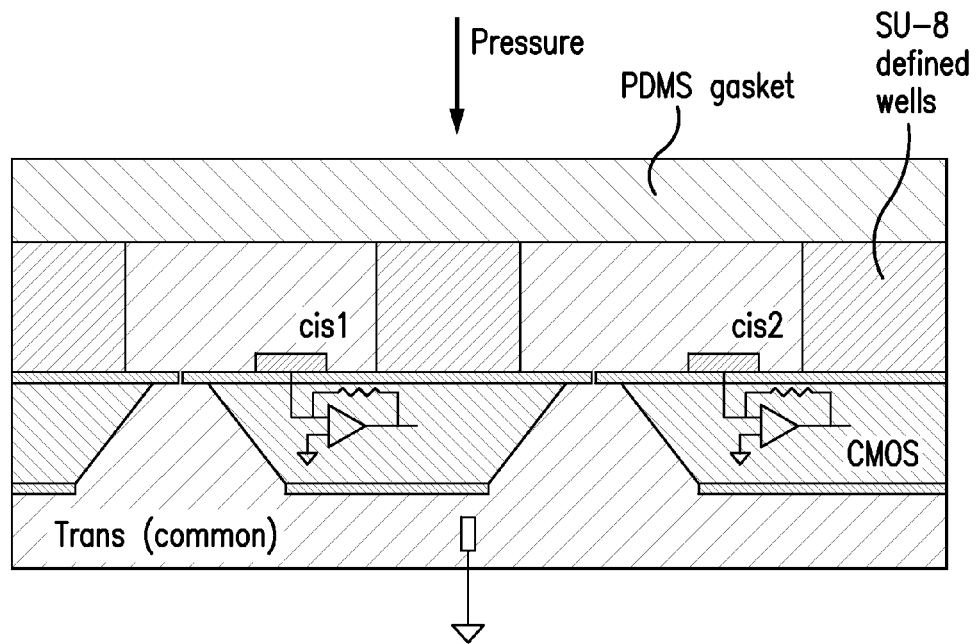
FIG. 18 is diagram of a single chip packaging having multiple nanopores in accordance with some embodiments of the disclosed subject matter.
Figure 19:
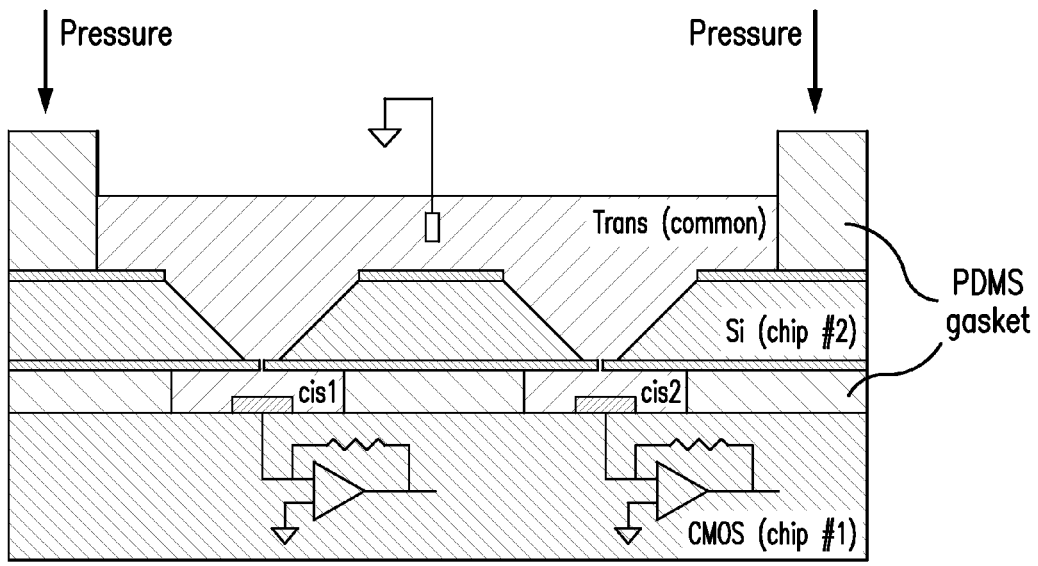
FIG. 19 is diagram of a two-chip packaging having multiple nanopores in accordance with some embodiments of the disclosed subject matter.

In accordance with some embodiments, a method for fabrication and packaging multiple pores on the same chip is disclosed. For example, multiple pores can be formed in the one-chip topology shown in FIG. 14 in which nanopores are integrated directly into the die with fluidics on either side of the chip. One approach for integrating multiple pores is shown in FIG. 18 for the purpose of illustration and not limitation. In this case, wells of SU-8 photoresist can be used to isolate individual nanopores from each other. In this case, since electrical isolation is necessary between the multiple cis reservoirs, a PDMS cap can be used to seal the wells for measurement after the introduction of reagents as shown in FIG. 18. In accordance with this method the full integration of 64 nanopores onto the same 5-mm-by-5-mm die can be provided. In another embodiment, a two-chip multi-well implementation using the same CNP design is provided, as shown in FIG. 19 for the purpose of illustration and not limitation.

In some embodiments, the CNP platform in accordance with the disclosed subject matter also allows the integration of biological nanopores. While solid-state pores have distinct advantages in manufacturability that is compatible with electronics processing (which was exploited as described above) and high pore signal levels, biological nanopores, including but not limited to alpha-Hemolysin (αHL) or MspA, have several distinct advantages, including high reproducibility and slower DNA translocation rates due to stronger DNA-pore interactions.

In some embodiments, the biological nanopores can be created in lipid membranes (typically 1,2-diphytanoyl-sn-glycero-3-phosphocholine (DPhPC)) formed over a hole in a hydrophobic membrane between two fluid cells. The conductance between the two chambers of the cell is monitored while the membrane protein is added to one of the wells, which is then immediate flushed once incorporation is detected.

The dielectric membranes described above can also be used as solid supports for lipid bilayers with the creation of moderately larger holes, over which the lipid bilayer is formed. For example, planar bilayer lipid membranes (BLMs) have been engineered with different protein channels on patterned solid supports with nanopatterned holes (~100 nm in diameter), as well as tethering BLMs directly onto gold surfaces through a self-assembled monolayer assembly.

To study the contiguousness of these bilayer films, the fluorescent recover after photobleaching (FRAP) technique was used. Fluorescein-DHPE was dried along with the DOPC, before reconstitution in water at 2.5 mg/ml, after which they were extruded through porous membranes to form 50-100 nm diameter unilamellar vesicles. FIG. 20c shows some of the results of these FRAP studies. The studies indicate the formation of contiguous BLMs with a diffusion coefficient of 4 $\mu m^2/s$ on nanopatterned substrates, and BLMs formed on SAM-gold assemblies with a coefficient of 0.8 $\mu m^2/s$. Both fall within the ideal diffusion range of 0.1-10 $\mu m^2/s$ representative of well-formed BLMs. Electrical characterizations of these BLMs indicate a high impedance membrane with a 1.4 G$\Omega$-mm$^2$ resistance, suitable for further electrical analysis of biological nanopores formed in the membranes.

Figure 20A:
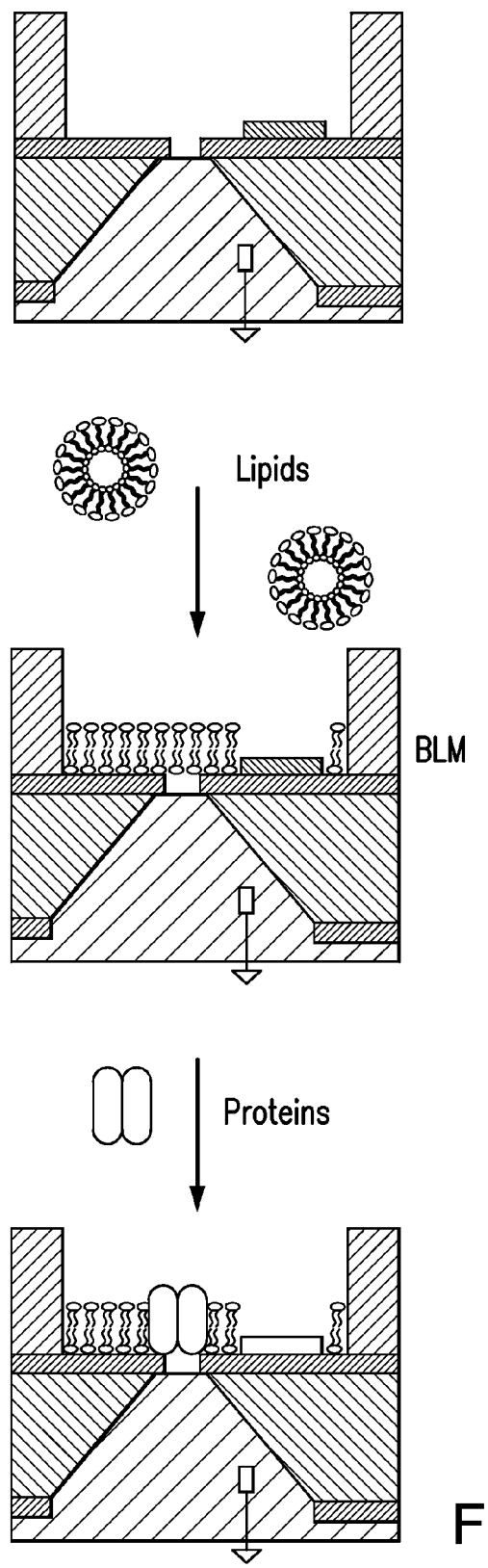

For the purpose of illustration and not limitation, FIG. 20 shows the integration of biological nanopores using the CNP platforms described above with holes in dielectric membranes by building lipid bilayers on the surface of the CNP designs. The protein nanopore formed over the nitride membrane approach to be employed here is shown in FIG. 20a. In this case, slighter larger holes will be formed in the silicon nitride membrane (on the order of 100-250 nm) than were used for direct nanopore integration described above. αHL can be used, monitoring the conductance during incorporation to ensure single channel introduction, and immediately washing after channel formation. For fabricating multiple channels on the same chip, a voltage bias can be used to slow down incorporation, which can allow the bias to dynamically change after incorporation in an individual channel to prevent multiple incorporation.

Figure 20B:
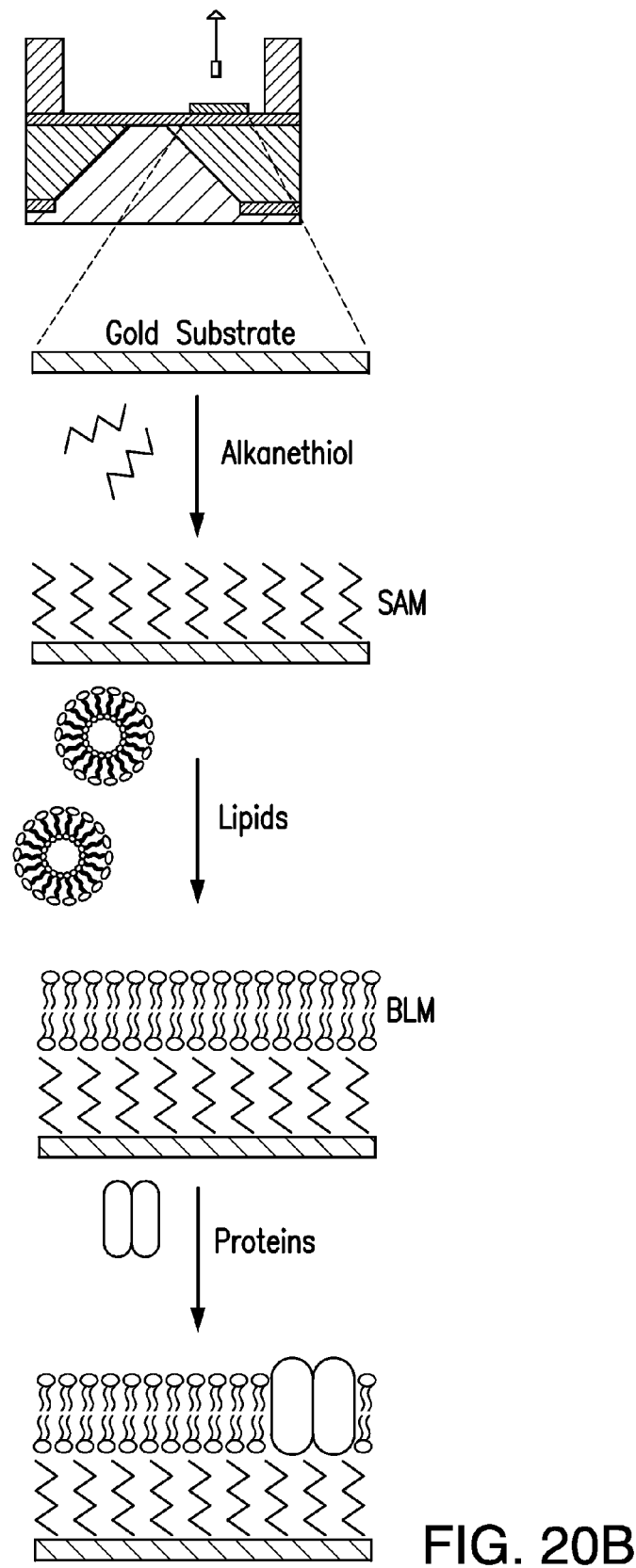

In accordance with some embodiments, the integration of biological channel proteins using the CNPs platform described above with tethered BLMs is provided. The protein nanopore formed over a SAM approach to be employed here is shown in FIG. 20b. In this case, the surface electrode is post-processed with a gold coating rather than silver, and is functionalized with a self-assembled monolayer (SAM), which provides an alternative surface for fluid lipid bilayer formation. Alkanethiols are one such material that readily forms SAMs on gold, producing a substrate that is both electrically conducting and conducive for lipid bilayer formation. Proteins within planar lipid bilayers can be formed on a SAM-gold assembly. In this arrangement there need not be electrolyte on the back side of the chip; the trans reservoir will be the liquid confined between the lipid bilayer and the gold surface, while the cis reservoir will be on the top side of the BLM.

In accordance with some embodiments, a "two-chip" biological nanopore embodiment is provided. Such an embodiment is similar to the two-chip solid-state nanopore embodiment described above and shown in FIG. 9, but the membrane is a self-assembled lipid bilayer instead of a dielectric material. In one embodiment, the lipid bilayer is in contact with the surface of the integrated circuit chip.

In accordance with one aspect of the disclosed subject matter, the membrane can be any suitable membrane, such as but not limited to a silicon nitride or graphene membrane. Graphene membranes are very thin pore substrate and can probe at subnanometer length scales. The pore can be fabricated using any known technique such as through electron-beam ablation, which allows pores to be reliably and repeatably made to diameters as small as 2 nm.

As described above, an integrated preamplifier for nanopore sensors in accordance with the disclosed subject matter significantly reduces electrical parasitics present in measurements with external amplifiers. The new arrangement can extend the useful bandwidth of nanopore sensors beyond 1 MHz, as compared to today's limits of sub-100 kHz measurements. Such bandwidths are highly relevant to achieve the time resolution useful for DNA sequencing with nanopores. For example, single-molecule events as short as 1 μs can be observed. Additionally, the monolithic integration of solid-state nanopores into a commercial CMOS die can provide ultrasensitive single-molecule biosensing applications.

Furthermore, the use of integrated preamplifier for nanopore sensors in accordance with the disclosed subject matter significantly reduces the cost and size as compared to the use of known external amplifiers. For example, the superior electrical performance is obtained with an integrated amplifier that consumes an area of only 0.2 mm$^2$ on a CMOS chip compared with a rack-mounted >10-kg Axopatch amplifier. At the same time, an Axopatch can cost more than about $25,000 while the amplifier proposed here could cost about $0.10 in volume manufacturing.

While the above disclosed subject matter focused on the measurement of the conductance of the pore, one of ordinary skill in the art will recognize that other sensing modalities are conceivable. For example but without limitation, monitoring tunneling currents with transverse electrodes, measuring capacitances through nanoelectrodes, and measuring conductance of graphene nanoribbons or carbon nanotubes positioned in close proximity to pores can also benefit from the integrated measurement electronics described herein. Measuring the ionic conductance of other transmembrane proteins is another application of the disclosed subject matter. Additional opportunities presented by the high-bandwidth bioelectronic interfaces described herein include the ability to study fast reaction kinetics, single-molecule transport phenomena, or fast conformational changes of macromolecules. Single-molecule recapture systems or closed-loop electrostatic traps would similarly benefit from high-bandwidth sensing.

EXAMPLES

CMOS-Integrated Nanopore Platform (CNP)

The amplifier is a custom integrated circuit implemented using a commercial IBM 0.13 μm bulk CMOS mixed-signal process. The amplifier die is wirebonded to a 272-pin ball-grid array (BGA) package. Dam-and-fill doughnut epoxy encapsulation (available commercially as Hysol FP4451 dam and FP4650 fill) covers the exposed gold wirebonds, leaving the die surface exposed.

After doughnut encapsulation, the chip surface is further passivated with SU-8. Under yellow light, a drop of SU-8 2015 (commercially available from Microchem) is manually applied to the surface of the amplifier die, filling the 300 μm-deep cavity formed by the epoxy dam. A light vacuum is applied in a dessicator for 15 minutes, followed by an overnight prebake in an oven at 80° C. The chip is exposed in an MJB-3 UV contact aligner using a chrome-on-glass mask, 2,000 mW/cm$^2$ dose, and 360 nm long-pass UV filter (commercially available from Omega Optical). A post-exposure-bake for 30 min at 50° C. and development in SU-8 Developer (commercially available from Microchem) yields a layer of SU-8 approximately 200-300 μm thick with 300 μm square openings surrounding the 100×100 μm square electrodes.

A watertight fluid chamber is constructed by fastening a 1-cm segment from a polypropylene tube to the top of the BGA package using PDMS (commercially available as Sylgard 184, Dow Corning). Additionally, KWIK-CAST (commercially available from World Precision Instruments) is applied on the die surface leaving only one amplifier channel exposed.

After packaging the die, the aluminum is etched from the exposed surface electrodes by pipetting 500 μL of Aluminum Etchant Type A (commercially available from Transene, Danvers, Mass.) into the fluid chamber for several minutes, followed by multiple rinses with DI water.

The chip is mounted on a circuit board, power is applied, and digital logic is applied which shunts the amplifier's feedback element, $C_F$, clamping the electrodes at a constant voltage and providing a path for it to sink several microamperes of current. A small volume (~1 mL) of silver electroplating solution containing potassium silver cyanide (available from Transene, Danvers, Mass.), is added to the fluid chamber, and a silver wire counterelectrode is attached to a Keithley 2400 I-V meter and placed in the solution. The voltage is adjusted to achieve a counterelectrode current of 1 μA for several minutes, resulting in a deposition of approximately 10 microns of silver onto the electrode. After electroplating, the chamber is rinsed multiple times with deionized water.

The silver microelectrodes are converted to Ag/AgCl pseudo-reference electrodes by applying a drop of 10 μL 50 mM $FeCl_3$ to the surface for 30 seconds. After several hours of experiments, the chlorination typically need to be repeated. The chlorination can be repeated several times before the silver electrode is exhausted.

Nanopores in ultrathin silicon nitride membranes are fabricated as known in the art. Briefly, a 500 μm thick <100> silicon wafer with Sum of thermal oxide is coated with 25 nm of low-stress LPCVD SiN. Standard UV photolithography is used to pattern square openings on one side of the wafer, through which the $SiO_2$/SiN is etched using $SF_6$ plasma. The photoresist is stripped, and an anisotropic KOH etch followed by removal of the $SiO_2$ layer results in ~50×50 μm free-standing windows on the reverse side of the wafer.

A film of PMMA is spun onto the membrane side of the window, and electron-beam lithography is used to pattern a small 200×200 nm square opening. A $SF_6$ plasma etch locally thins the SiN to approximately 10 nm. The PMMA is removed by incubation in acetone. A single nanopore is drilled through the thinned region of the nitride membrane using a JEOL 2010F HR-TEM.

The nanopore chip is cleaned in piranha acid using a procedure known in the art. After rinsing and drying the membrane, it is immediately mounted onto a custom Teflon fluid cell using KWIK-CAST (available from World Precision Instruments). Additionally, KWIK-CAST is carefully painted over the majority of the membrane-facing side of the chip, leaving an exposed <1 mm$^2$ area around the membrane (see FIG. 5e).

When testing with the Axopatch 200B, the Teflon cell is placed into a mating fluid cell containing 1M KCl 10 mM Tris buffer, pH 8.0. Inside a Faraday cage, two homemade Ag/AgCl pellet electrodes are connected to the headstage input and ground, respectively.

For testing with the CNP amplifier, the circuit board is placed in small aluminum box and the lower (trans) reservoir is filled with 500 uL 1M KCl, pH 8.0. The upper (cis) chamber within the Teflon cell is filled with 200 uL electrolyte, and the cell is placed into the amplifier chamber. An Ag/AgCl pellet electrode is placed in the cis chamber. The amplifier input voltage is held constant, while the DC potential of the opposing electrode is varied to apply a bias across the nanopore.

The preamplifier with its attached fluid chamber is mounted in a compression-mount BGA socket (commercially available from Emulation Technologies) on a 15×13 cm circuit board, and placed in a small aluminum box. The circuit board contains DC voltage regulation, biasing circuitry, analog signal buffering and filters, all of which are carefully designed for low-noise operation. This preamplifier board is powered from four AAA batteries and its digital interfaces are galvanically isolated. A second interface board outside the aluminum box hosts digital isolators, antialiasing filters (4-pole differential Bessel filter, $f_c$=1 MHz) and data converters (operating at either 2.5 MS/s or 4 MS/s), as well as an FPGA module (commercially available as Opal Kelly XEM3010) with a high-speed USB interface. The data acquisition and control of the system is managed in real-time through a graphical interface written in Matlab.

The data is processed using Matlab software. Traces are generally digitally filtered with a 128-tap finite-impulse-response low-pass filter to a desired signal bandwidth, while retaining the 2-4 MS/s sample rate. Events are typically identified with a two-state thresholding algorithm in Matlab, but for traces with low SNR, a modified algorithm is used to identify the events. First, samples are identified whose value is more than 5 standard deviations below the mean open pore current. Next, a local search finds the nearest sample points at which the current is above the open pore current. Finally, event edge times are assigned at the first and last points within these bounds that the signal is more than 4 standard deviations from the baseline current.

Noise Measurements in CMOS-Integrated Nanopore Platform (CNP)

Figure 21A:
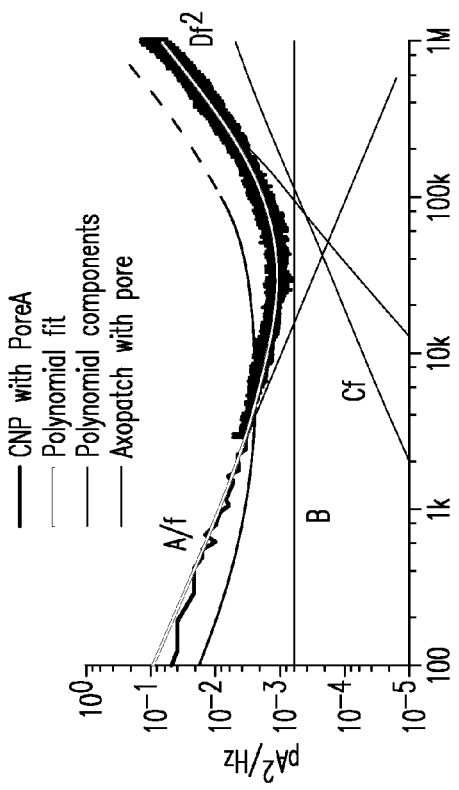
FIG. 21A-I shows graphs of the current noise measurements in accordance with some embodiments of the disclosed subject matter.

The measured open-headstage noise spectrum of the CNP system ($C_F$=0.15 pF, 1 MHz 4-pole Bessel filter, $f_s$=4 MS/s) is shown in FIG. 21a, alongside a measurement of the baseline noise for a comparable configuration of the Axopatch 200B (whole-cell mode with β=1, 100 kHz 4-pole Bessel filter, $f_s$=250 kS/s). At measurement bandwidths below 10 kHz, the noise of the Axopatch is lower than the CNP, owing to the 10 fA/√Hz current noise of the CNP's on-chip current source (FIG. 7) as compared to 5.7 fA/√Hz from a discrete 500 MΩ feedback resistor in the Axopatch. However, for B>10 kHz, the CNP delivers significantly lower noise floors. For the highest bandwidth supported by the Axopatch (B=100 kHz), the CNP has a noise floor of 3.2 $pA_{RMS}$, compared to 9 $pA_{RMS}$ for the Axopatch. At the highest bandwidth characterized for the CNP (B=1 MHz), the noise level is 24 $pA_{RMS}$, in contrast with 247 $pA_{RMS}$ modeled by extrapolating the Axopatch response beyond its supported range.

Figure 21C:
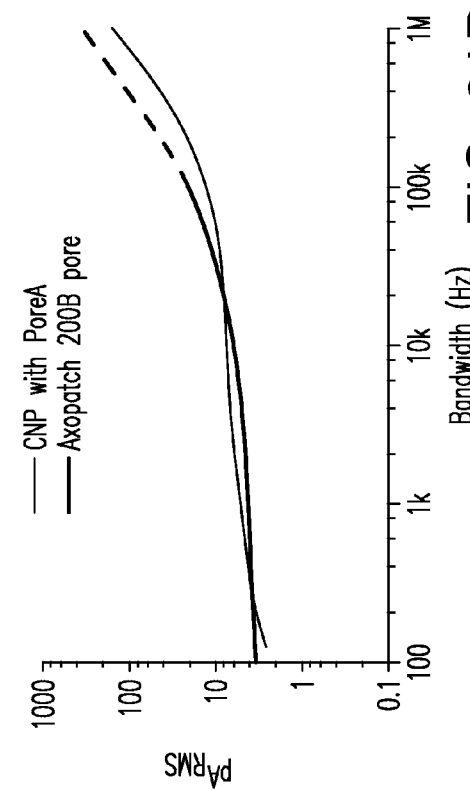
Figure 21B:
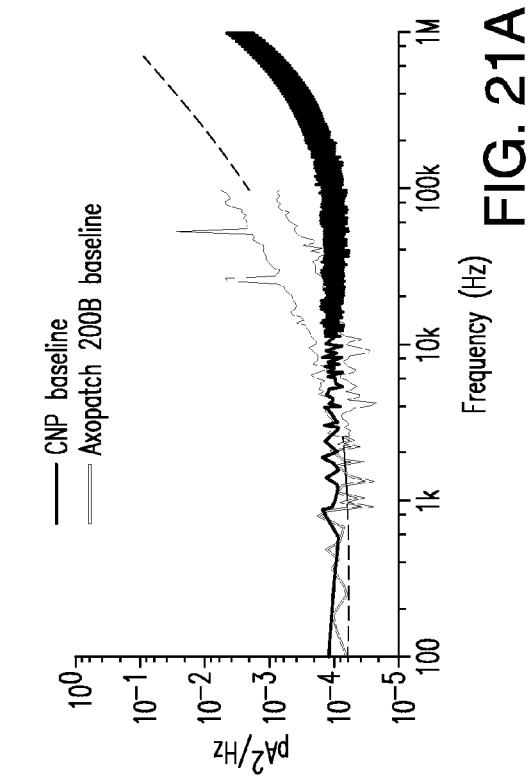
Figure 21D:
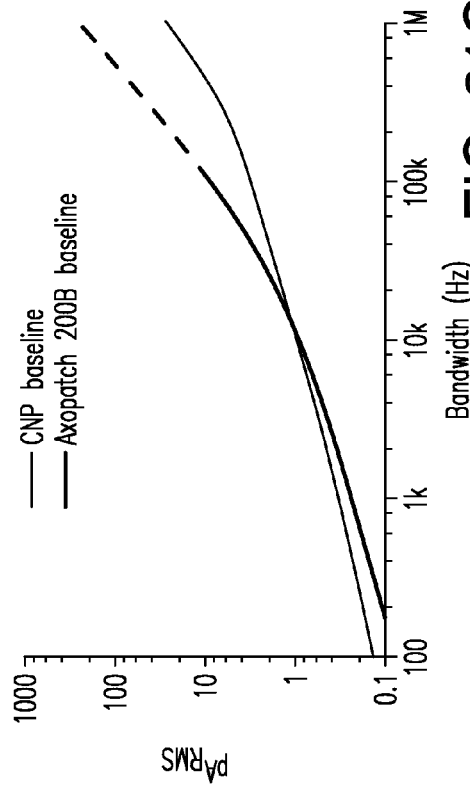
Figure 21E:
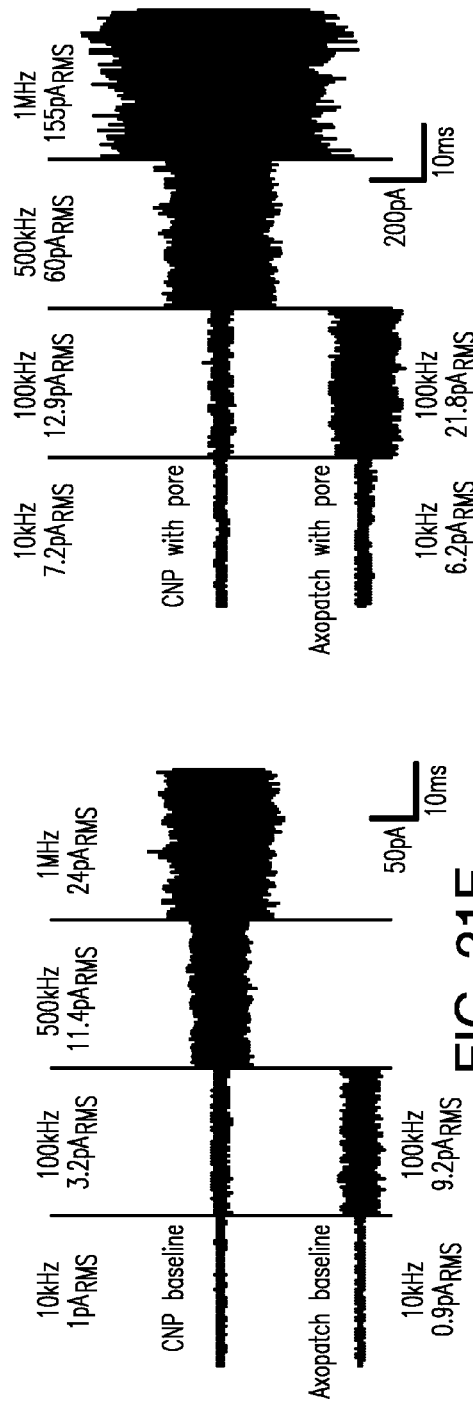

When a nanopore is connected to the amplifier input, the introduction of 1/f noise and membrane capacitance raises the noise spectrum above the open-headstage baseline, as shown in FIG. 21b (a polynomial fit is also shown to $i_n^2$=A/f+B+Cf+Df$^2$, where f is the frequency (Hz) and A, B, C, and D are fitting parameters). Approximately 15 solid-state nanopores were measured with the CNP and significant pore-to-pore SNR variability was observed, due both to variations in the pore geometry and in $C_M$. In the discussions that follow, data from two representative pore devices ("PoreA" and "PoreB") are selected for analysis. PoreA (d=4.9 nm, $C_M$=6 pF, $\Delta I$=882 pA at 400 mV) has lower membrane capacitance than PoreB (d=3.5 nm, $C_M$=25 pF, $\Delta I$=840 pA at 400 mV). FIG. 21c shows root-mean-squared (RMS) current noise as a function of bandwidth, corresponding to the signals in the plot of FIG. 21a and FIG. 21d shows the RMS current noise corresponding to the signal in FIG. 21b along with measured RMS current noise for a similar nanopore measured with the Axopatch 200B with the same configuration as FIG. 21a. FIGS. 21e and f are current traces corresponding to the points in FIGS. 21c and d.

Figure 21F:
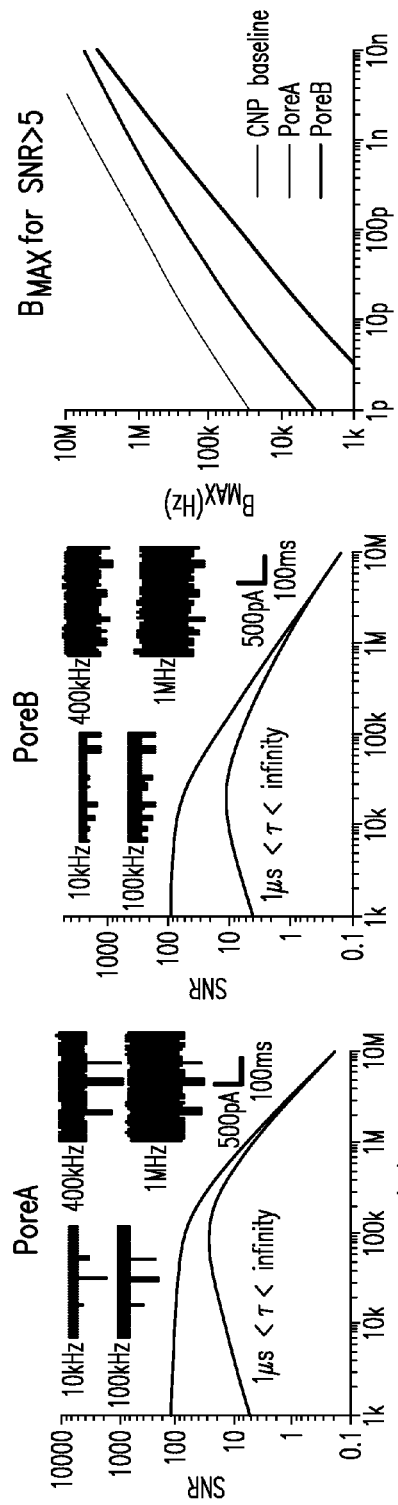

For the lowest-capacitance devices measured, such as PoreA, noise levels in the CNP are demonstrated at 12.9 $pA_{RMS}$ and 155 $pA_{RMS}$ for bandwidths of 100 kHz and 1 MHz, respectively (FIG. 21f). Measured comparisons are shown with the Axopatch up to 100 kHz. For B=100 kHz, there is more than a factor-of-two reduction in input-referred noise power for the CNP. If the Axopatch could be measured at higher bandwidths, there would be a factor-of-six noise power difference at 1 MHz.

Aside from the overall lower noise at high frequencies, polynomial fits to the noise power spectrum (FIG. 21b) are notable for the absence of a significant linear component at moderate frequencies (>1 kHz), which dominate the high-frequency noise in earlier reports. A linear spectral component can have several possible sources, but the CNP's improvement is likely due to the high-quality dielectric properties of the thermal $SiO_2$ passivation of the nanopore support chip.

Maximizing Signal Strength in CMOS-Integrated Nanopore Platform (CNP)

Maximizing the SNR involves both minimizing noise and maximizing the amplitude of the signal. The measured current signal is given by $\Delta I = V_{BIAS} \Delta G$, where $V_{BIAS}$ is the applied bias and $\Delta G$ is the change in ionic conductivity caused by the presence of a molecule. Recent results with thin silicon nitride nanopores demonstrate current pulses from dsDNA as large as 4 nA using 4-nm-diameter pores in 8-nm-thick membranes at 300 mV bias.

For the measurements presented here, free-standing 25-nm-thick silicon nitride membranes are locally thinned using an $SF_6$ plasma, yielding small membrane regions approximately 10-15 nm thick. A single nanopore is fabricated in a thinned region using a transmission electron microscope. Fabricated pores ranged from 2-6 nm in diameter, but the best signals were obtained for 3.5-4 nm pores. All experiments were performed using 1M KCl buffered with Tris to pH 8.0.

Figure 21G:
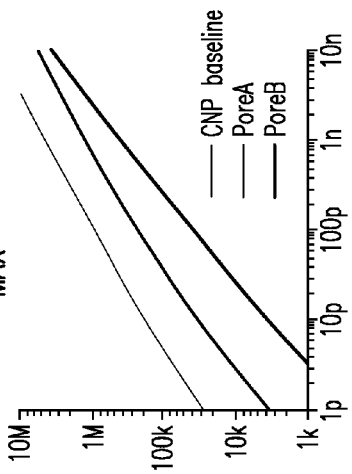
Figure 21H:
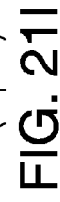
Figure 21I:

FIGS. 21g and h shows plots of SNR (as introduced above) for both PoreA and PoreB as a function of measurement bandwidth. For PoreA, $C_M$=6 pF and $\Delta I$=814 pA (400 bp DNA, 300 mV, N=330). For PoreB, $C_M$=25 pF and $\Delta I$=840 pA (50 bp DNA, 400 mV, N=2,974). As dwell times vary significantly, the SNR is shown for a range of $1 \mu s < \tau < \infty$. For PoreA, SNR is maintained above 10 beyond 600 kHz measurement bandwidth, and above 5 beyond 1 MHz. For PoreB, SNR values of 10 and 5 are maintained up to 160 kHz and 320 kHz, respectively. FIG. 21i, which plots $B_{MAX}$ for SNR>5 as a function of signal amplitude $\Delta I$, shows that in the limit of very small $C_M$, the baseline amplifier noise floor corresponds to usable measurement bandwidth of several MHz.

Short DNA Measurements

Figure 22:
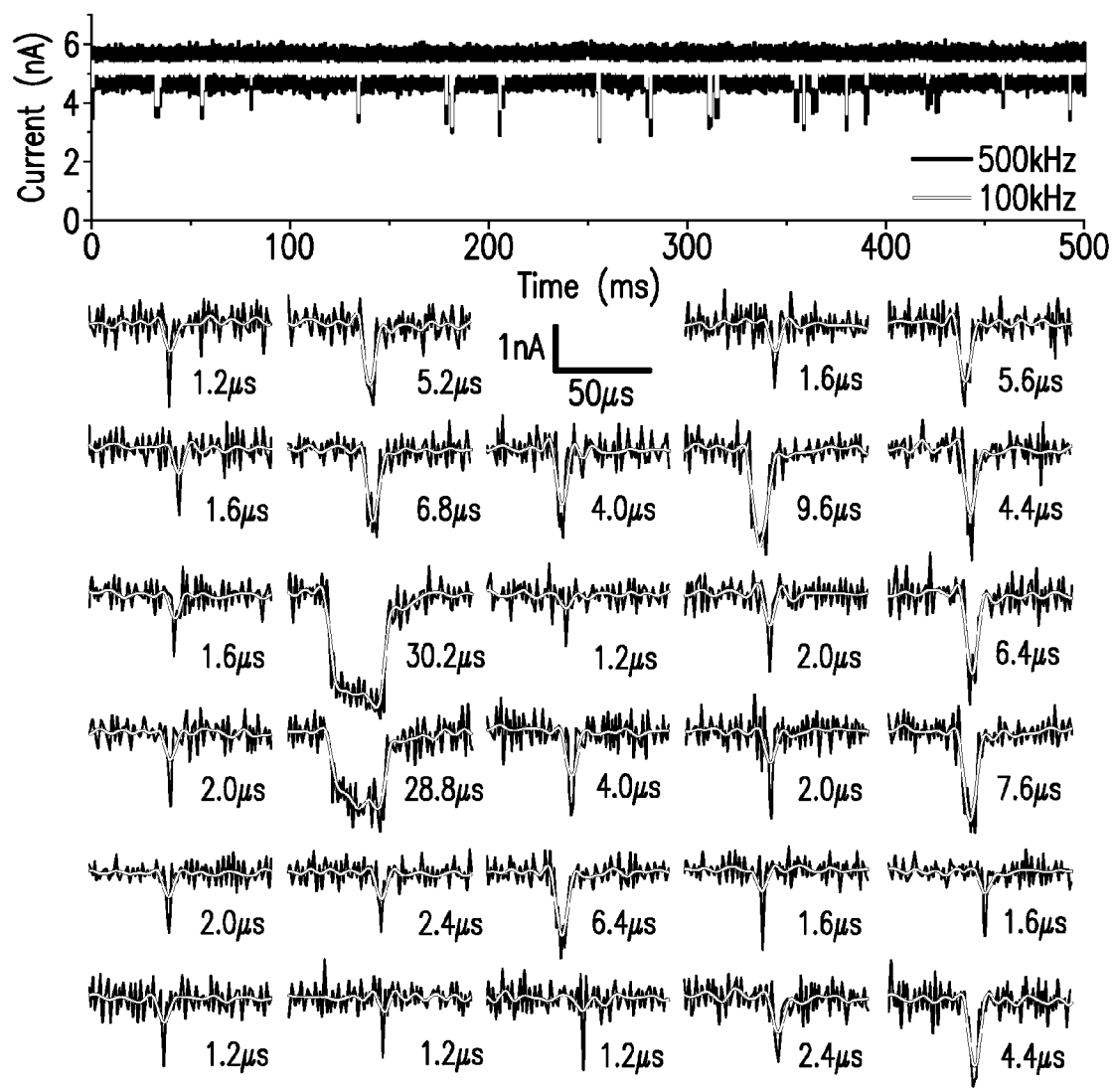
FIG. 22 is a continuous trace recorded for 25 bp dsDNA fragments for a pore (i.e. PoreB) using a CNP platform at a bias of 600 mV in accordance with some embodiments of the disclosed subject matter.

As an example of the short timescales observable with the CNP, FIG. 22 shows a current trace measured for PoreB with 25 bp dsDNA. The pore was biased at 600 mV, digitized at 2.5 MS/s, and then digitally filtered to both 500 kHz (blue) and 100 kHz (red) bandwidths. The 500 kHz trace represents the maximum bandwidth in which SNR>5 for PoreB in these conditions ($\Delta I$=1.3 nA, N=1,307), and the 100 kHz trace is included as a comparison to the supported bandwidth of alternative platforms. In the 0.5-second trace shown, 29 pulses are visible, ranging in duration from 1.2 µs to 30.2 µs. Points are recorded at intervals of 0.4 µs but the rise and fall times are approximately 1 µs and 5 µs for the 500 kHz trace and 100 kHz trace, respectively. Accordingly, events shorter than 10 µs are clearly visible in the 500 kHz trace but their amplitude is attenuated at 100 kHz. Notably, the data presented here was taken at room temperature.

DNA Translocation Statistics

Figure 23A:
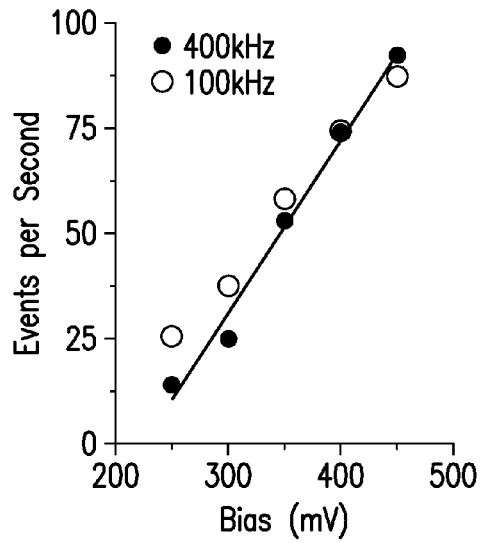
FIG. 23A-D is a collection of events showing the impact of higher measurement bandwidth on the quality of statistics gathered for nanopore sensors in accordance with some embodiments of the disclosed subject matter.
Figure 23B:
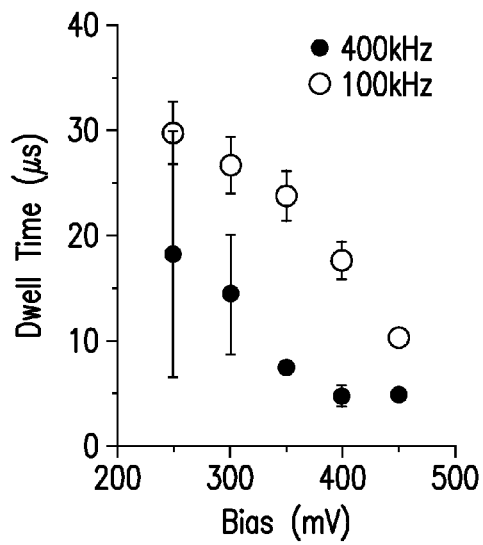
Figure 23C:
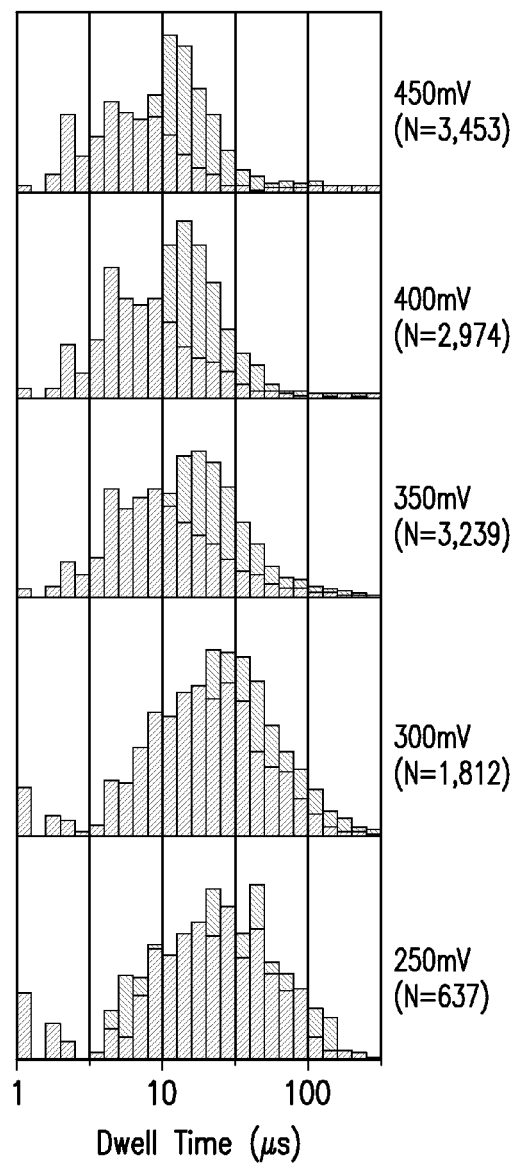
Figure 23D:
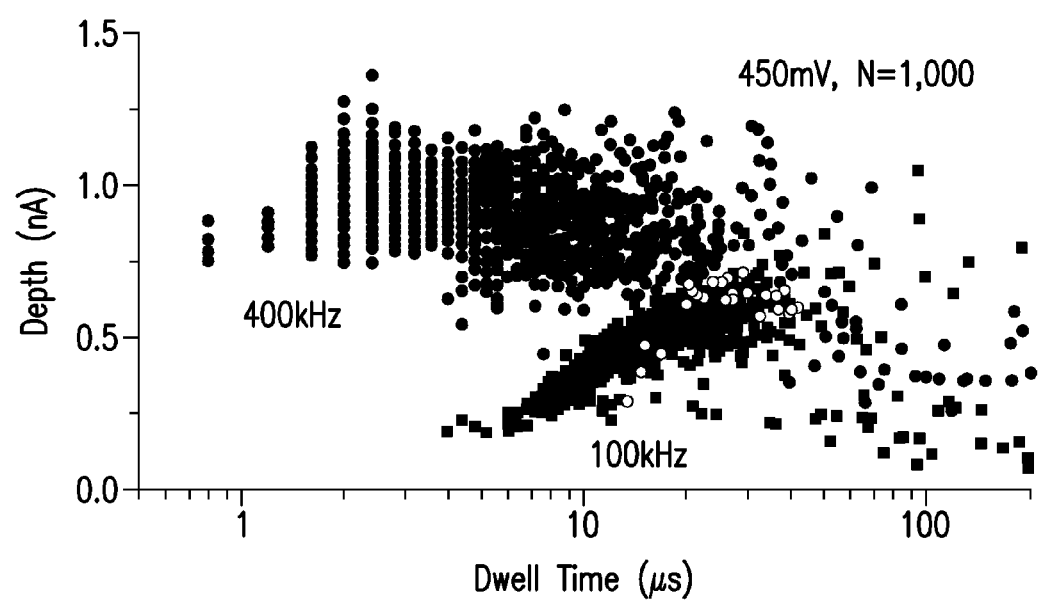

Extended signal bandwidth also gives the ability to consider the statistics of shorter duration events than have been previously observed. At 3.5 nm in diameter, PoreB is small enough that oligomer translocation times are dominated by surface interactions rather than electrophoretic forces. As such, a wide variance in translocation times is observed. FIG. 23 shows a dataset of the durations and depths of events seen for 50 bp DNA at 250-450 mV bias, for both 400 kHz (blue) and 100 kHz (red) signal bandwidths. FIG. 23a shows the event rate as a function of applied bias. The event rate scales roughly linearly above a 200 mV threshold, suggesting a diffusion-limited capture regime. Event rates are similar for the two bandwidths except that at 100 kHz some events are lost at high bias (due to filtering), while at 400 kHz some events are lost at low bias (due to noise). FIG. 23b shows the most probable dwell time as a function of applied potential. Events become faster with higher bias but measured dwell times saturate near the temporal resolution of the selected filters. FIG. 23c shows histograms of events at applied potentials from 250-450 mV, for the two bandwidths. FIG. 23d is a scatter plot of events observed at 450 mV bias. Events shorter than 10 µs are severely distorted and attenuated by a 100 kHz measurement bandwidth.

Observed event rates for the two bandwidths are similar, showing a roughly linear trend with bias voltage, above a threshold of 200 mV. However, the event durations decrease with applied bias, and events as short as 2 µs are clearly distinguished at 400 kHz, while at 100 kHz events shorter than 10 µs are strongly attenuated and their apparent dwell time saturates near the temporal response of the filter. This distortion has a marked effect on the observed statistics of the events, exaggerating the duration of short events in the 100 kHz dataset (FIG. 23b-c). At 400-450 mV, events continue to be observed below the 2.5 µs response of the 400 kHz filter, implying the existence of sub-microsecond events which could be observed if the membrane capacitance of PoreB were further decreased.

Intra-Event Translocation Dynamics

At low bandwidths and sample rates, nanopore-DNA interactions can appear to have uniform blockade levels, but in a number of cases events have been observed with multiple current levels which correspond to folded polymers, hybridized probe molecules, or conformations of larger proteins. Statistical analyses of the durations of nanopore events have shown that within the typical operating range of these sensors, several different biophysical processes can be observed. For larger nanopores, translocation times can be dominated by electrophoretic forces, while for smaller-diameter pores it can take longer for a polymer to diffuse into a proper orientation for an end to be threaded through the pore. The event duration can be further extended by physiochemical interactions between the molecule and the pore surface.

FIG. 24 presents a dataset of events measured for PoreB with 50 bp DNA fragments at 500 mV bias. FIG. 24a is an illustration of the sequential processes of nanopore translocation. First a molecule diffuses near the pore, where it is captured by the electric field. The molecule is trapped at the mouth of the pore until it finds a conformation which allows one of its ends to thread through the pore. FIG. 24b shows typical signals observed for 50 bp dsDNA fragments with PoreB (3.5 nm) at 500 mV bias. The events have a characteristic shallow level followed by a deeper tail. FIG. 24c is histogram of ΔI event depths (N=3955) for 50 bp DNA at 500 mV bias. The depth of the whole events and the depth of the last 2 μs of each event have distinct distributions. FIG. 24d is a plot of the most probable ΔI for whole events, along with the most probable ΔI for the first and last 2 μs of an event. The depth of the last 2 μs retains a linear relationship with voltage up to 500 mV, while the earlier sections of the event become shallower at high bias. This can be indicative of molecular dynamics at high electric fields which suppress polymer diffusion and extend the duration of the 'Capture' phase relative to the 'Threading' phase.

For this high bias, events are commonly observed to have a characteristic shallow blockage level, followed by a deeper tail immediately before completion. This bears a strong resemblance to signals previously observed for hairpin DNA molecules with protein nanopores. One reasonable explanation for this intra-event structure is the multi-state process illustrated in FIG. 24a. A diffusing molecule is captured by the nanopore, but the strong electric field and relatively stiff molecule (a 50 bp DNA molecule is approximately 15 nm long, with a radius of curvature of 4 nm) prevent the molecule from quickly finding an appropriate conformation to thread through the 3.5 nm nanopore. The presence of the molecule trapped at the mouth of the nanopore causes the initial shallow blockage. When the molecule eventually threads successfully, it translocates to the opposing chamber, causing a deeper blockage.

Figure 24A:
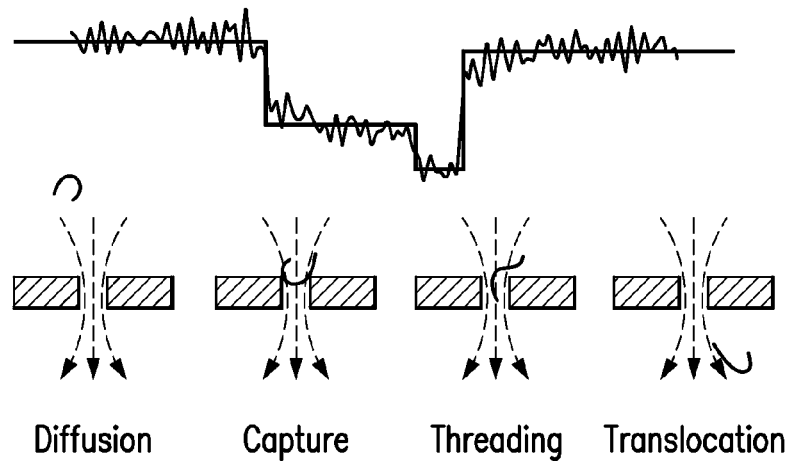
FIG. 24A-D is a presentation of intra-event structure observed with short oligomers and small nanopores in accordance with some embodiments of the disclosed subject matter.
Figure 24B:
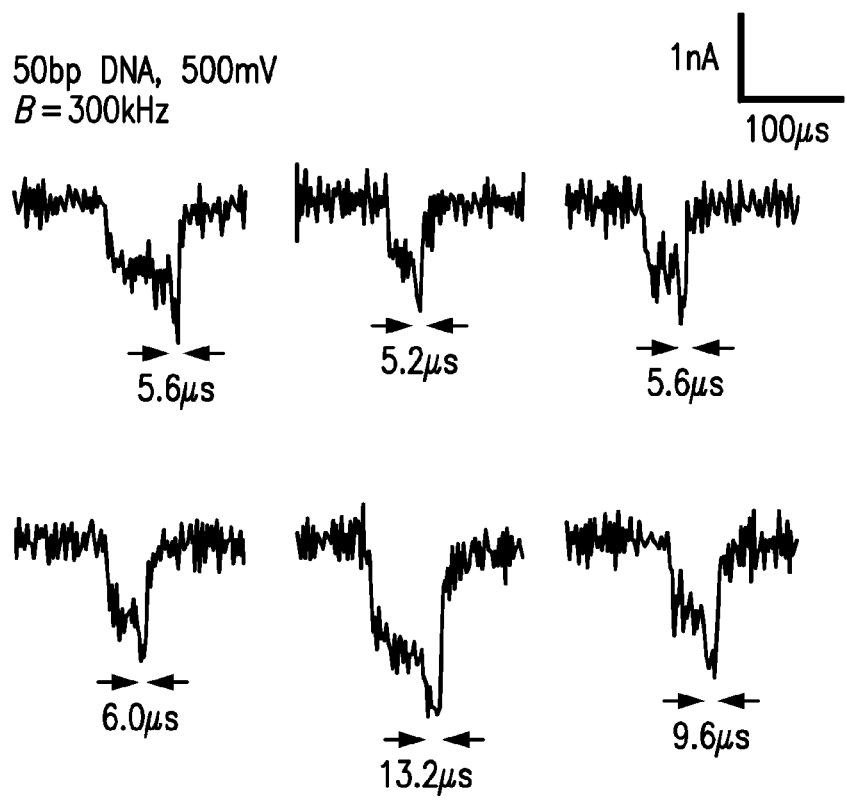
Figure 24C:
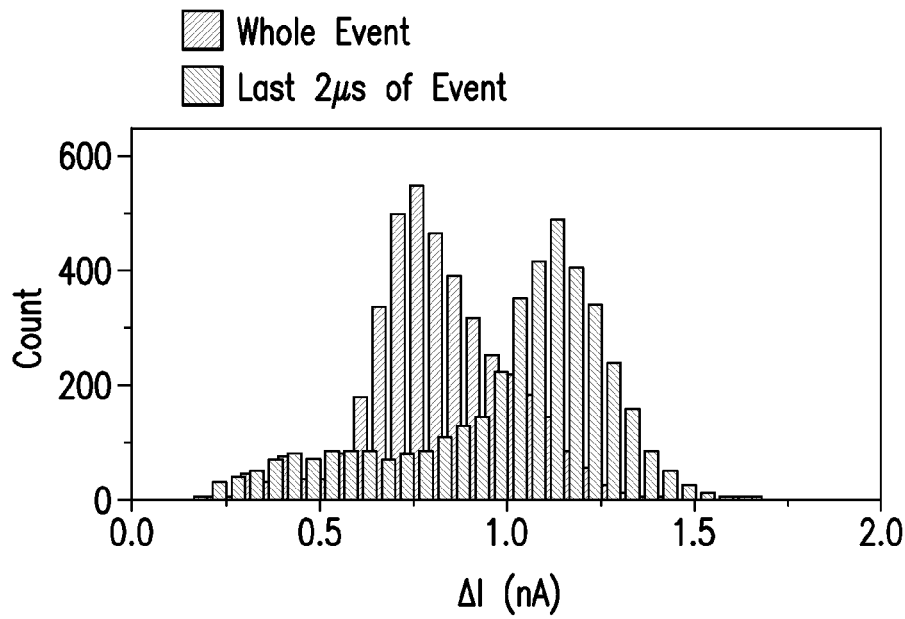
Figure 24D:
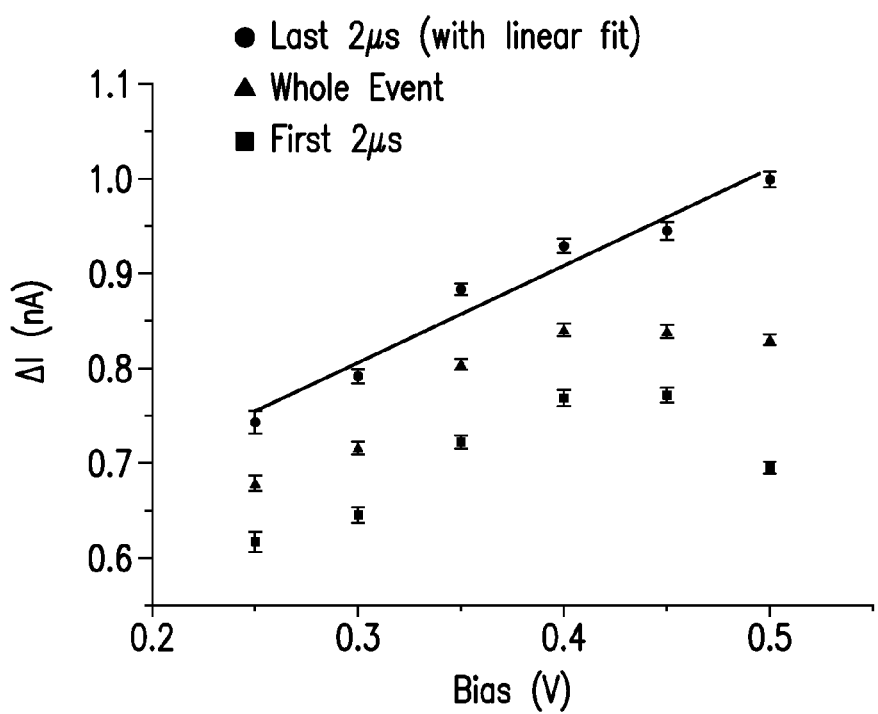

In this dataset the duration of the deeper tail is often less than 10 μs, and it is commonly obscured in lower-bandwidth measurements. The relative depth of the tail can be analyzed statistically by considering a histogram of the mean depths of each whole event, as compared to the depth of last 2 μs of each event. As shown in FIG. 24c, these blockage levels show markedly different distributions, with centers at 0.75 nA and 1.1 nA, respectively. Interestingly, the depth of the last 2 μs shows a more linear relationship with bias voltage than does the depth of events as a whole (FIG. 24d). This supports that the tail corresponds to the translocation of a molecule, and that at lower bias voltages the 'capture' state is simply too short to contribute significantly to observed events.

While the disclosed subject matter is described herein in terms of certain embodiments, those skilled in the art will recognize that various modifications and improvements can be made to the application without departing from the scope thereof. Thus, it is intended that the present application include modifications and variations that are within the scope of the appended claims and their equivalents. Moreover, although individual features of one embodiment of the application can be discussed herein or shown in the drawings of one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the application such that the application upon should be recognized as also specifically directed to other embodiments having any other possible combinations. Thus, the foregoing description of specific embodiments of the application has been presented for purposes of illustration and description. It is not intended to be exhaustive or to limit the application to those embodiments disclosed.

The invention claimed is:

1. A method for detecting a single-molecule using an integrated circuit which includes at least one membrane having a nanopore located between first and second reservoirs and a low-noise preamplifier having an electrode formed on the surface thereof, comprising:
   passing a target molecule through the nanopore; and
   measuring a current through the nanopore to detect the presence of a biomolecular entity, if any,
   wherein the first reservoir is adjacent a first side of the preamplifier and the second reservoir is adjacent an opposing second side of the preamplifier.

2. The method of claim 1, wherein the preamplifier comprises a low-noise multi-channel CMOS preamplifier.

3. The method of claim 1, wherein the electrode is selected from the group consisting of Ag/AgCl, platinum, gold, and un-chlorinated silver.

4. The method of claim 1, wherein the nanopore is positioned on a silicon chip adjacent to the preamplifier.

5. The method of claim 1, wherein the nanopore comprises a nanopore directly integrated onto the preamplifier.

6. The method of claim 1, wherein the nanopore comprises a solid state nanopore.

7. The method of claim 1, wherein the nanopore comprises a biological nanopore.

8. The method of claim 7, wherein the membrane is a lipid bilayer.

9. The method of claim 1, wherein the electrode is in direct contact with one of the first and second reservoirs.

10. The method of claim 1, wherein the integrated circuit comprises a plurality of nanopores.

11. An integrated circuit for single-molecule detection, comprising:
   at least one membrane having a nanopore located between first and second reservoirs;
   a low-noise preamplifier for measuring the change in pore current upon passing a target entity through the nanopore, the first reservoir adjacent a first side of the preamplifier and the second reservoir adjacent an opposing second side of the preamplifier, wherein the preamplifier has at least one electrode formed on the surface thereof.

12. The integrated circuit of claim 11, wherein the preamplifier comprises a low-noise multi-channel CMOS preamplifier.

13. The integrated circuit of claim 11, wherein the electrode is selected from the group consisting of Ag/AgCl, platinum, gold, and un-chlorinated silver.

14. The integrated circuit of claim 11, wherein the nanopore is located through a silicon chip adjacent to the preamplifier.

15. The integrated circuit of claim 11, wherein the nanopore comprises a nanopore directly integrated onto the preamplifier.

16. The integrated circuit of claim 11, wherein the nanopore comprises a solid state nanopore.

17. The integrated circuit of claim 11, wherein the nanopore comprises a biological nanopore.

18. The integrated circuit of claim 17, wherein the membrane is a lipid bilayer.

19. The integrated circuit of claim 11, wherein the electrode is in direct contact with one of the first and second reservoirs.

20. The integrated circuit of claim 11, wherein the integrated circuit comprises a plurality of nanopores.

* * * * *